(12) United States Patent
Feke et al.

(10) Patent No.: US 8,203,132 B2
(45) Date of Patent: Jun. 19, 2012

(54) APPARATUS AND METHOD FOR IMAGING IONIZING RADIATION

(75) Inventors: Gilbert Feke, Durham, CT (US);
Douglas O. Wood, North Haven, CT (US); Douglas L. Vizard, Durham, CT (US)

(73) Assignee: Carestream Health, Inc., Rochester, NY (US)

( * ) Notice: Subject to any disclaimer, the term of this patent is extended or adjusted under 35 U.S.C. 154(b) by 722 days.

(21) Appl. No.: 12/324,092

(22) Filed: Nov. 26, 2008

(65) Prior Publication Data

US 2009/0114860 A1 May 7, 2009

Related U.S. Application Data

(63) Continuation-in-part of application No. 11/221,530, filed on Sep. 8, 2005, now Pat. No. 7,734,325.

(60) Provisional application No. 61/024,621, filed on Jan. 30, 2008.

(51) Int. Cl.
*G01N 23/04* (2006.01)
(52) U.S. Cl. ....................................................... 250/583
(58) Field of Classification Search ............. 250/370.09, 250/580–587; 600/407, 440
See application file for complete search history.

(56) References Cited

U.S. PATENT DOCUMENTS

| | | | |
|---|---|---|---|
| 1,609,703 A | 12/1926 | Eggert et al. |
| 3,717,764 A | 2/1973 | Fujimura et al. |
| 3,936,644 A | 2/1976 | Rabatin |
| 4,028,550 A | 6/1977 | Weiss et al. |
| 4,088,894 A | 5/1978 | Rabatin |
| 4,107,070 A | 8/1978 | Everts et al. |
| 4,208,470 A | 6/1980 | Rabatin |
| 4,232,227 A | 11/1980 | Finkenzeller et al. |
| 4,394,737 A | 7/1983 | Komaki et al. |
| 4,446,365 A | 5/1984 | Ong et al. |
| 4,675,529 A | 6/1987 | Kushida |
| 4,710,637 A | 12/1987 | Luckey et al. |
| 4,829,188 A | 5/1989 | Shinomiya et al. |
| 4,870,279 A | 9/1989 | Cueman et al. |
| 4,891,527 A | 1/1990 | Rabatin |
| 4,898,175 A | 2/1990 | Noguchi |
| 5,069,982 A | 12/1991 | Zegarski |
| 5,307,804 A | 5/1994 | Bonnet |
| 5,501,225 A | 3/1996 | Wilson |

(Continued)

FOREIGN PATENT DOCUMENTS

EP    1 111 625 A2    6/2001

(Continued)

OTHER PUBLICATIONS

Cleare et al., "An Experimental Study of the Mottle Produced by X-Ray Intensifying Screens," The Am. J. of Roent. and Rad. Physics, vol. 88, No. 1, pp. 168-174, Jul. 1962.

(Continued)

*Primary Examiner* — David Porta
*Assistant Examiner* — Marcus Taningco

(57) ABSTRACT

A system and method are disclosed for capturing a radiographic or autoradiographic image of an object, in which a support member is provided to receive the object in an immobilized state; a phosphor screen is provided to transduce ionizing radiation from the source to visible light; film or a digital capture device is provided for capturing an image using the visible light; and the phosphor screen is moved incrementally to facilitate reduction of phosphor screen mottle.

30 Claims, 24 Drawing Sheets

U.S. PATENT DOCUMENTS

| | | | |
|---|---|---|---|
| 5,534,709 A | 7/1996 | Yoshimoto et al. | |
| 5,650,135 A | 7/1997 | Contag et al. | |
| 5,663,005 A | 9/1997 | Dooms et al. | |
| 5,717,791 A | 2/1998 | Labaere et al. | |
| 5,730,701 A | 3/1998 | Furukawa et al. | |
| 5,748,768 A | 5/1998 | Sivers et al. | |
| 5,830,629 A | 11/1998 | Vizard et al. | |
| 6,227,704 B1 | 5/2001 | Bani-Hashemi et al. | |
| 6,229,873 B1 | 5/2001 | Bani-Hashemi et al. | |
| 6,268,613 B1 * | 7/2001 | Cantu et al. | 250/584 |
| 6,269,177 B1 | 7/2001 | Dewaele et al. | |
| 6,278,765 B1 | 8/2001 | Berliner | |
| 6,346,707 B1 | 2/2002 | Vizard et al. | |
| 6,379,044 B1 | 4/2002 | Vastenaeken et al. | |
| 6,416,800 B1 | 7/2002 | Weber et al. | |
| 6,424,750 B1 | 7/2002 | Colbeth et al. | |
| 6,444,988 B1 | 9/2002 | Vizard | |
| 6,447,163 B1 | 9/2002 | Bani-Hashemi et al. | |
| 6,459,094 B1 | 10/2002 | Wang et al. | |
| 6,473,489 B2 | 10/2002 | Bani-Hashemi et al. | |
| 6,495,812 B1 | 12/2002 | Wurm et al. | |
| 6,531,225 B1 | 3/2003 | Homme et al. | |
| 6,615,063 B1 | 9/2003 | Ntziachristos et al. | |
| 6,686,200 B1 | 2/2004 | Dong et al. | |
| 6,762,420 B2 | 7/2004 | Homme et al. | |
| 6,948,502 B2 | 9/2005 | Berger et al. | |
| 7,113,217 B2 | 9/2006 | Nilson et al. | |
| 7,190,991 B2 | 3/2007 | Cable et al. | |
| 7,198,404 B2 | 4/2007 | Navab et al. | |
| 7,338,651 B2 | 3/2008 | Bornhop et al. | |
| 7,394,053 B2 | 7/2008 | Frangioni et al. | |
| 7,406,967 B2 | 8/2008 | Callaway | |
| 7,734,325 B2 | 6/2010 | Vizard et al. | |
| 2001/0012386 A1 | 8/2001 | Struye et al. | |
| 2003/0011701 A1 | 1/2003 | Nilson et al. | |
| 2003/0082104 A1 | 5/2003 | Mertelmeier | |
| 2003/0187344 A1 | 10/2003 | Nilson et al. | |
| 2003/0211158 A1 | 11/2003 | Frechet et al. | |
| 2004/0004193 A1 | 1/2004 | Nilson et al. | |
| 2004/0089817 A1 | 5/2004 | Long et al. | |
| 2004/0199067 A1 | 10/2004 | Bock et al. | |
| 2004/0202360 A1 | 10/2004 | Besson | |
| 2004/0249260 A1 | 12/2004 | Wang et al. | |
| 2005/0028482 A1 | 2/2005 | Cable et al. | |
| 2005/0122529 A1 | 6/2005 | Kim et al. | |
| 2005/0148846 A1 | 7/2005 | Cable et al. | |
| 2005/0175538 A1 | 8/2005 | Coquoz et al. | |
| 2005/0237423 A1 | 10/2005 | Nilson et al. | |
| 2006/0064000 A1 | 3/2006 | Vizard et al. | |
| 2006/0111613 A1 | 5/2006 | Boutillette et al. | |
| 2006/0118742 A1 | 6/2006 | Levenson et al. | |
| 2006/0173354 A1 | 8/2006 | Ntziachristos et al. | |
| 2006/0210135 A1 | 9/2006 | Kanegae | |
| 2006/0293396 A1 | 12/2006 | Bringley et al. | |
| 2007/0016077 A1 | 1/2007 | Nakaoka et al. | |
| 2007/0063154 A1 | 3/2007 | Chen et al. | |
| 2007/0087445 A1 | 4/2007 | Tearney et al. | |
| 2007/0217713 A1 | 9/2007 | Milanfar et al. | |
| 2007/0238656 A1 | 10/2007 | Harder et al. | |
| 2007/0238957 A1 | 10/2007 | Yared | |
| 2007/0281322 A1 | 12/2007 | Jaffe et al. | |
| 2008/0045797 A1 | 2/2008 | Yasushi et al. | |
| 2008/0049893 A1 | 2/2008 | Bartzke et al. | |
| 2008/0197296 A1 | 8/2008 | Uematsu | |
| 2008/0281322 A1 | 11/2008 | Sherman et al. | |
| 2009/0086908 A1 | 4/2009 | Harder et al. | |
| 2009/0159805 A1 | 6/2009 | Feke et al. | |
| 2009/0238434 A1 | 9/2009 | Feke et al. | |
| 2010/0022866 A1 | 1/2010 | Feke et al. | |

FOREIGN PATENT DOCUMENTS

| | | |
|---|---|---|
| EP | 1 304 070 A2 | 4/2003 |
| EP | 1 619 548 A2 | 1/2006 |
| JP | 58-17544 U | 7/1981 |
| JP | 02-031144 | 2/1990 |
| JP | 02-052246 | 2/1990 |
| JP | 09-309845 | 12/1997 |
| JP | 11-244220 | 9/1999 |
| JP | 2001-255607 | 9/2001 |
| JP | 2001-299786 | 10/2001 |
| JP | 2003-028995 | 1/2003 |
| JP | 2004-121289 | 4/2004 |
| JP | 2005-049341 | 2/2005 |
| JP | 2005-164577 | 6/2005 |
| WO | 2004/081865 A2 | 9/2004 |
| WO | 2004/089204 A1 | 10/2004 |
| WO | 2004/108902 A2 | 12/2004 |
| WO | 2005/027730 A2 | 3/2005 |
| WO | 2007/032940 A2 | 3/2007 |

OTHER PUBLICATIONS

User's Guide for KODAK Imagst Station 2000R, Aug. 2002, (172 pages).

User's Guide for KODAK Image Station 2000MM, Nov. 2003 (168 pages).

Corresponding WO = PCT/us2005/032504, International Preliminary Report on Patentability, dated Mar. 27, 2007, 8 pages.

Corresponding CN = CN 200580031808.5—SIPO First Office Action dated Dec. 4, 2009. 14 pages.

International Search Report, International Application No. PCT/US2005/032504, dated Dec. 23, 2005.

International Search Report, International Application No. PCT/US2008/010304, dated Dec. 8, 2008.

International Search Report, International Application No. PCT/US2009/000457, dated Aug. 21, 2009.

Hamamatsu Photonics K.K., Catalog No. SFAS0017E06, X-Ray Line Scan Camera, Jun. 2010, 4 pages.

Hamamatsu Photonics K.K., Publication No. TMCP1031E04, X-Ray Scinitllator, Jun. 2009, 4 pages.

EP Sear Report, Application No. EP10012074, dated Apr. 18, 2011, 2 pages.

Research Takes Many Directions, Science, vol. 303, No. 5657, Jan. 23, 2004. Advertisement (2 pages).

Sage, Linda, "The Bare Bones of Animal Imaging", *The Scientist*, vol. 19, Issue 4, Feb. 28, 2005. (4 pages).

"Monomolecular Multimodal Fluorescence-Radiosotope Imaging Agents", Bioconjugate Chemistry, 16(5), pp. 1232-1239, 2005.

CosmoBio report, Mar. 2004, No. 43, "Kodak Image Station 2000MM". (English translation of p. 18—5 pages).

CosmoBio report, Mar. 2004, No. 43, "Kodak Image Station 2000MM". (JP language—Foreign, 13 pages).

Kodak Image Station 2000MM Multimodal Imaging System, Internet web address: http://www.kodak.com/US/en/health/scientific/products/imgstation2000MM/index.shtml—Sep. 16, 2004. (1 page).

Hussain et al., Enhanced Oral Uptake of Tomato Lectin-Conjugated Nanoparticles in the Rat, Pharmaceutical Research, vol. 14, No. 5, 1997, pp. 613-618.

V.P. Torchilin, Polymer-coated long-circulating microparticulate pharmaceuticals, J. Microencapsulation, 1998, vol. 15, No. 1, pp. 1-19.

Alyautdin et al., Delivery of Loperamide Across the Blood-Brain Barrier with Polysorbate 80-Coated Polybutylcyanoacrylate Nanoparticles, Pharmaceutical Research, vol. 14, No. 3, 1997, pp. 325-328.

Y. Kwon et al., Enhanced antigen presentation and immunostimulation of dendritic cells using acid-degradable cationic nanoparticles, Journal of Controlled Release 105, 2005, pp. 199-212.

Harlow et al., Antibodies—A Laboratory Manual, Chapter 5—Immunizations, 1988, pp. 91-113.

Winter et al., Man-made antibodies, Nature—vol. 349, Jan. 24, 1991, pp. 293-299.

Köhler et al., Derivation of specific antibody-producing tissue culture and tumor lines by cell fusion, Medical Research Council Laboratory of Molecular Biology, Cambridge, Eur. J. Immunol., 1976, vol. 6, pp. 511-519.

LoBuglio et al., Mouse/human chimeric conoclonal antibody in man: Kinetics and immune response, Proc. Natl. Acad. Sci., vol. 86, Jun. 1989 Immunology, pp. 4220-4224.

De Verdiè, et al., Reversion of multidrug resistence with polyalkycyanoacrylate nanoparticles: towards a mechanism of action, BJC British Journal of Cancer, 1997, vol. 76 (2), pp. 198-205.

Sharma et al., Novel Taxol® Formulation: Polyvinylpyrrolidone Nanoparticle-Encapsulated Taxol® for Drug Delivery in Cancer Therapy, Oncology Research, vol. 8, Nos. 7/8, pp. 281-286, 1986.

Zobel et al., Cationic Polyhexylcyanoacrylate Nanoparticles as Carriers for Antisense Oligonucleotides, Antisense & Nucleic Acid Drug Development, vol. 7, 1997, pp. 483-493.

Burke et al., Acid-Base Equilibria of Weak Polyelectrolytes in Multilayer Thin Films, Langmuir, 2003, vol. 19, No. 8, pp. 3297-3303.

Hrkach et al., Nanotechnology for biomaterials engineering; structural characterization of amphiphilic polymeric nanoparticles by $^1$H NMR spectroscopy, Biomaterials, vol. 18, No. 1, 1997, pp. 27-30.

G. Volkheimer, Ubersicht, Persorption von Mikropartikeln, Pathologies, 1993, vol. 14, pp. 247-252.

Moghimi et al., Nanomedicine: current status and future prospects, The FASEB Journal, vol. 19, Mar. 2005, pp. 311-330.

Soukchareun et al., Preparation and Characterization of Antisense Oligonucleotide—Peptide Hybrids Containing Viral Fusion Peptides, Bioconjugate Chem, 1995, vol. 6, pp. 43-53.

G. Kwon et al., Block copolymer micelles as long-circulating drug vehicles, Advanced Drug Delivery Reviews, vol. 16, 1995, pp. 295-309.

Labhasetwar et al., Nanoparticle drug delivery system for restenosis, Advanced Drug Delivery Reviews, vol. 24, 1997, pp. 63-85.

Nature Methods, "Harnessing multimodality to enhance quantification and reproducibility of in vivo molecular imaging data", by Gilbert D. Feke et al., Nov. 2008, 2 pages.

Biochem Biophys Res Commun, Inspiration for Life Science, "Anti Human Galectin 3 Polyelonal Antibody", by W. Zhu, 280:11831188, 2001, 2 pages.

IEEE Transactions on Nuclear Science, "Iodine 125 Imaging in Mice Using NaI(TI)/Flat Panel PMT Integral Assembly", by M.N. Cinti et al., vol. 54, No. 3, Jun. 2007, pp. 461-468.

Mat. Res. Soc. Symp. Proc., "Optimising of the Physico-Chemical Properties of a Novel Barium Sulphate Preparation for the X-Ray Examination Of The Intestine", by Barbara Laermann et al., vol. 550, 1999 Materials Research Society, pp. 59-64.

Am. Assoc. Phys. Med., "MicroCT scanner performance and considerations for vascular specimen imaging", by Michael Marxen et al., Med. Phys. 31 (2), Feb. 2004, pp. 305-313.

Rat Atlas Project, Internet Study: Hubei Bioinformatics and Molecular Imaging Key Laboratory, The Key Laboratory of Biomedical Photonics of Ministry of Education, College of Life Science and Technology, Huazhong University of Science and Technology, http://www.vch.org.cn/mice/method.aspx, printed from Internet on Sep. 12, 2011, (4 pages).

Kodak Image Station 2000MM Multi-Modal Imager, Kodak Scientific Imaging Systems-advertisment—Fall/2003 (2 pages).

Proceedings of the American Thoracic Society, "Micro-Computed Tomography of the Lungs and Pulmonary-Vascular System", by Erik L. Ritman, 2 pages 477-480, 2005.

The Journal of Nuclear Medicine, "Significance of Incidental 18F-FDG Accumulations in the Gastrointestical Tract in PET/CT: Correlation with Endoscopic and Histopathologic Results", by Ehab M. Kamel et al., vol. 45, No. 11, pp. 1804-1810, 2004.

P. Mitchell, "Picture Perfect: Imaging Gives Biomarkers New Look", *Pharma DD*, vol. 1, No. 3, pp. 1-5 (2006).

Virostko et al., Molecular Imaging, vol. 3, No. 4, Oct. 2004, pp. 333-342, Factors Influencing Quantification of in Vivo Bioluminescence Imaging: Application to Assessment of Pancreatic Islet Transplants.

Da Silva et al., ScienceDirect, Nuclear Instruments and Methods in Physics Research, Design of a small animal multimodality tomographer for X-ray and optical coupling: Theory and experiments, 2007, pp. 118-121.

Kruger et al., HYPR-spectral photoacoustic CT for preclinical imaging, Photons Plus Ultrasound Imaging and Sensing 2009, Proc. Of SPIE, vol. 7177, 10 pages.

\* cited by examiner

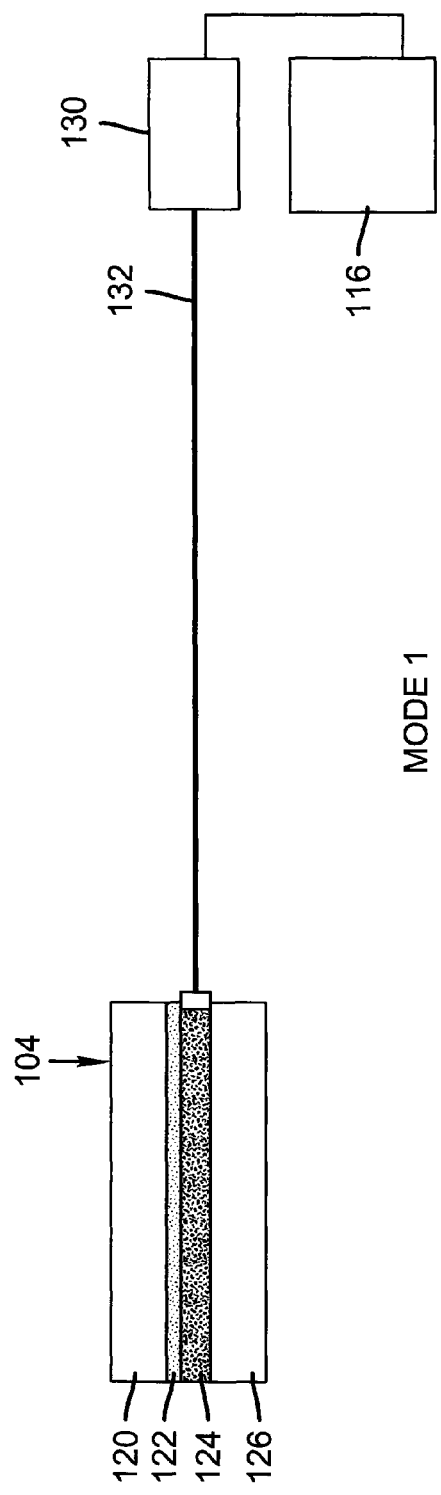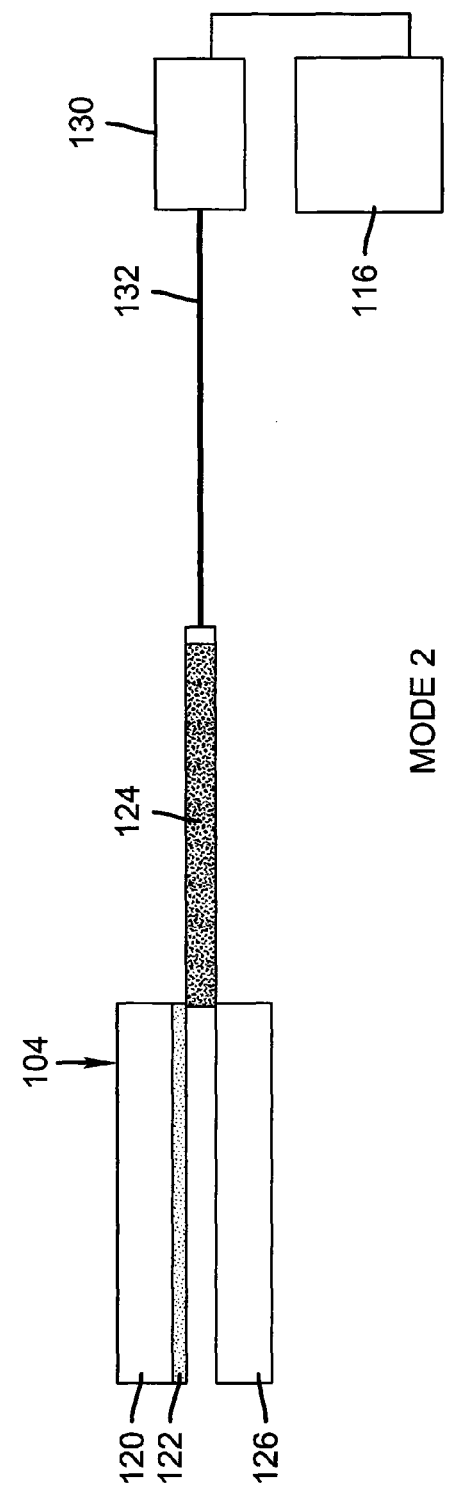
MODE 1
*FIG. 8A*
MODE 2
*FIG. 8B*

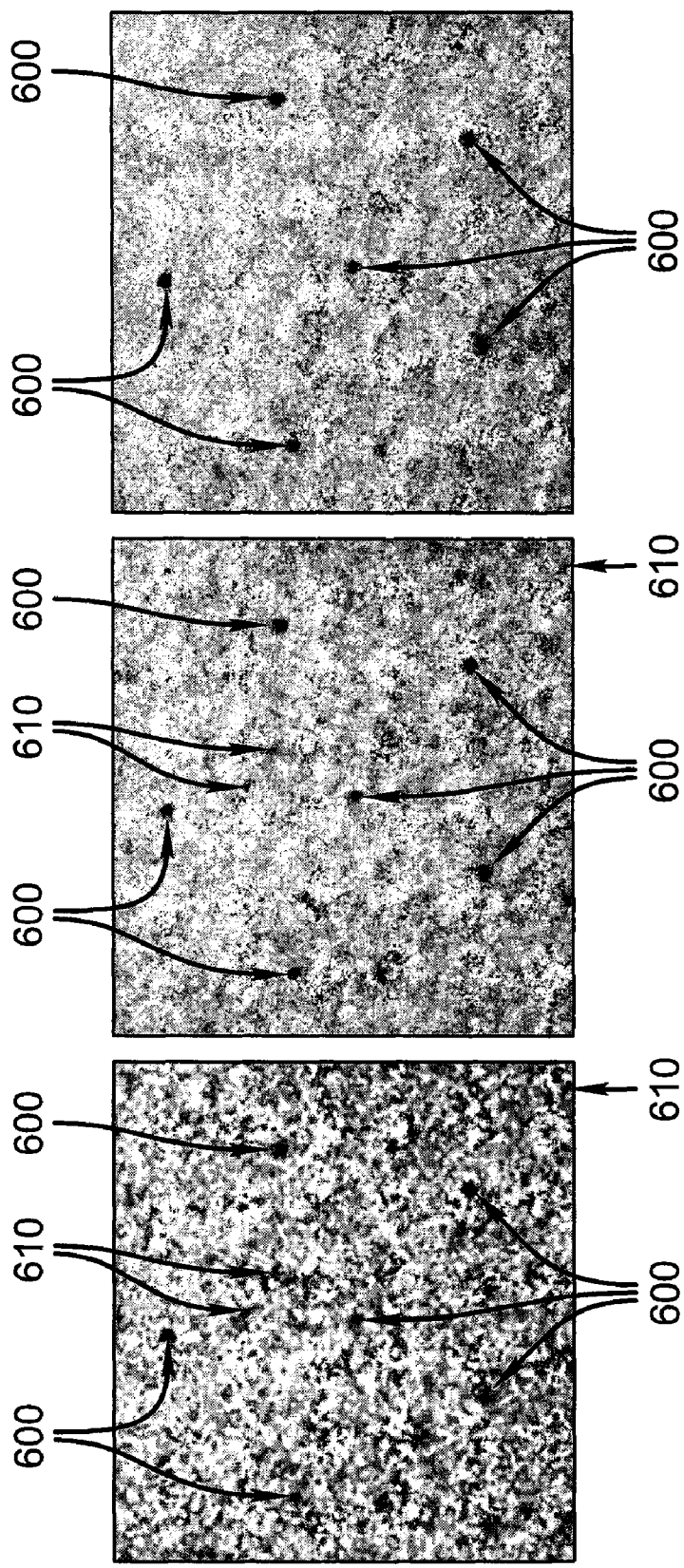

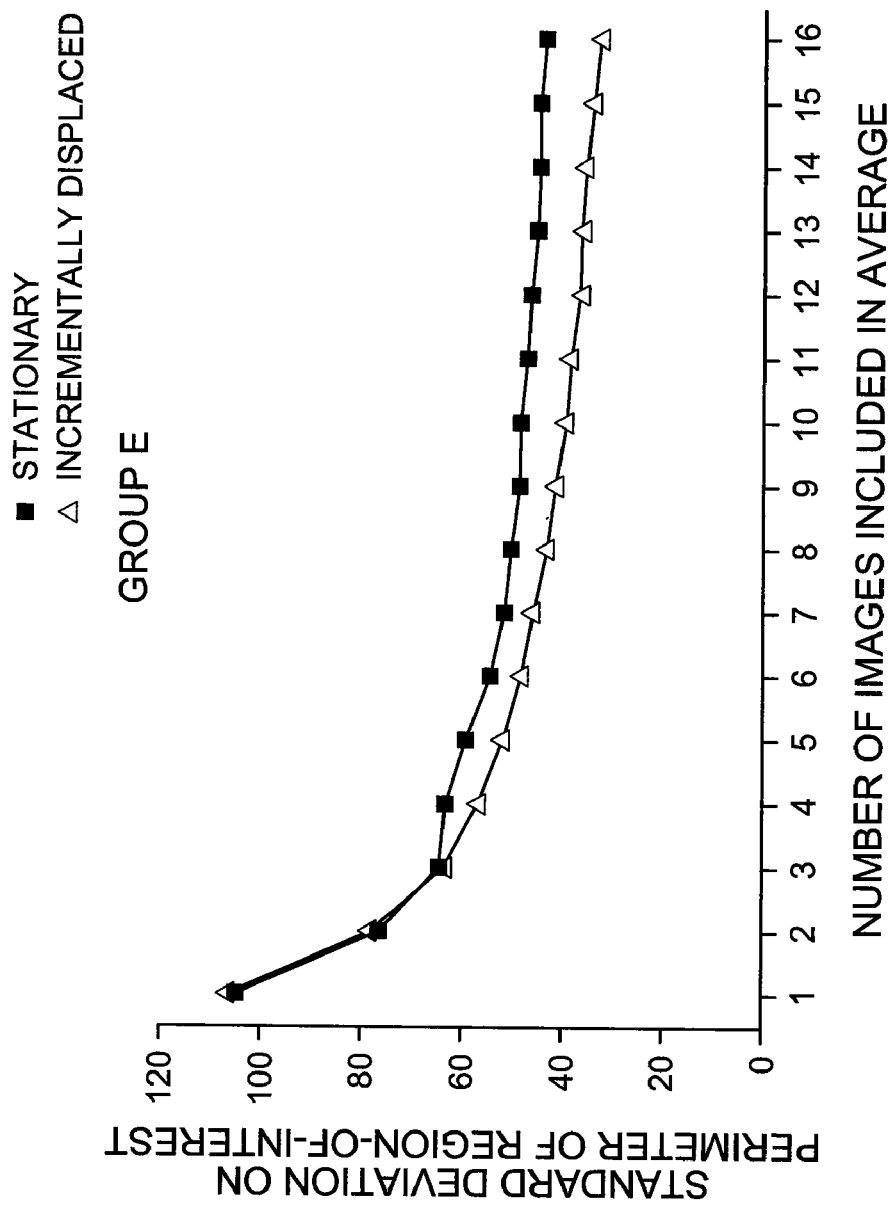

APPARATUS AND METHOD FOR IMAGING IONIZING RADIATION

CROSS REFERENCE TO RELATED APPLICATIONS

Priority is claimed to commonly assigned, copending provisional U.S. Patent Application Ser. Nos. 61/024,621 filed Jan. 30, 2008 by Feke et al entitled APPARATUS AND METHOD FOR MULTI-MODAL IMAGING, the disclosure of which is incorporated by reference into the present specification.

This application is a continuation-in-part of commonly assigned, copending U.S. patent application Ser. No. 11/221,530 filed Sep. 8, 2005 now U.S. Pat. No. 7,734,325 by Vizard et al entitled APPARATUS AND METHOD FOR MULTI-MODAL IMAGING, the disclosure of which is incorporated by reference into the present specification.

FIELD OF THE INVENTION

The invention relates generally to the elimination of the contribution of phosphor screen mottle to noise in phosphorescence detection in an ionizing radiation imaging system, such as a radiographic or autoradiographic imaging system.

BACKGROUND OF THE INVENTION

When imaging ionizing radiation with either film or digital detection means, phosphor screens are used to transduce the ionizing radiation to visible light. Phosphor screens have the inherent problem of contributing an artifact to the image called screen mottle. Screen mottle is the combined effect of macroscopic structural mottle and microscopic grain mottle, often lumped into the term "mottle". Generally, screen mottle contributes to the noise in phosphorescence detection, specifically high spatial frequency noise that is spatially fixed with respect to the detection means. It would be desirable to reduce or eliminate the contribution of mottle to noise in phosphorescence detection in an ionizing radiation imaging system, such as a radiographic or autoradiographic imaging system. This problem is particularly relevant to thin phosphor screens, as required for high spatial resolution radiography and autoradiography of small mammals, insects, fish, seeds, biopsy specimens, blots, gels, and the like, due to the small number of phosphor grains through a pixel equivalent column depth. Furthermore, this problem is particularly relevant in cases where a reduction in the dose of ionizing radiation to achieve a desired signal-to-noise ratio is desired, because a decrease in noise can compensate against a decrease in signal (due to reduction in dose) to maintain a desired signal-to-noise ratio.

A number of attempts to reduce or eliminate mottle have been reported in the literature. For example, reference may be made to Cleare et al, *The Am. J. of Roent. And Rad. Physics*, Vol. 88, No. 1, pp. 168-174 (July 1962); U.S. Published Patent Application 2006/0210135; and U.S. Pat. Nos. 1,609,703; 3,717,764; 3,936,644; 4,028,550; 4,088,894; 4,107,070; 4,208,470; 4,394,737; 4,710,637; 4,829,188; 4,891,527; 5,069,982; 5,663,005; 5,830,629; and 6,278,765. While some have achieved a measure of improvement, these attempted solutions have required added complexity and cost due to either the addition of complex materials, processes, or construction techniques, or the use of additional screens or layers. For example, some proposed solutions use a plurality of radiographic films or a plurality of phosphor screen layers. Some minimize the effective conversion efficiency of the screen or the screen speed or require the use of additional materials such as the embedding of metal strips. Others require adding extra materials such as brightening agents, combining $(Ba,Sr)F$, $(Cl,Br)$: $Eu^{+2}$ phosphors with particular rare earth oxyhalide phosphors, admixing a small amount of particular trivalent antimony compounds with the phosphor prior to screen preparation, or heating phosphor material while exposed to an oxygen-containing atmosphere. Still others require stabilization or a correction image data set.

U.S. Patent Application Publication No. 2007/0217713 and NewScientist.com news service, Dec. 21, 2007, describe a technique for creating higher resolution images by combining a plurality of lower resolution images. Forensic scientist and astronomers are currently applying the technique to security and astronomical images respectively, to produce higher resolution images. The method and software first acquire a series of lower resolution images while moving the subject and holding the capture device fixed or moving the capture device while holding the subject fixed. Then like pixels of the lower resolution images are combined to create a higher resolution image. Researchers are also applying this technique to radiography to obtain usable radiographic images that require less radiation dose. Radiographic images obtained in this fashion, however, are also subject to phosphor screen mottle, because the phosphor screen remains fixed in relationship to either the image capture device (whereby the mottle adds noise that is spatially fixed with respect to the plurality of images) or the subject (whereby the mottle adds noise that is spatially fixed with respect to the subject).

SUMMARY OF THE INVENTION

The present invention solves the problem caused by phosphor screen mottle essentially by virtue of blurring. Therefore, this invention solves the problem of phosphor screen mottle independently of the complexity and cost of the phosphor screen and the image capture process, so that even a simple an inexpensive phosphor screen and image capture process may be used in combination with this invention.

The present invention provides, in one embodiment, an apparatus and method for imaging an object, comprising a support member adapted to receive the object in an immobilized state; a phosphor screen adapted to transduce ionizing radiation from the object to visible light; and an imaging means for imaging the immobilized object. The apparatus may be radiographic and include a source of X rays or autoradiographic and image an object treated with radioisotopes. The imaging means may include features for pixelwise mathematical averaging of a sequence of individual images of the immobilized object acquired by use of the phosphor screen. The phosphor screen is incrementally displaced to facilitate reduction of phosphor screen mottle. The incremental displacement may be by a distance larger than the phosphor grain size and smaller than the difference between the physical size of the phosphor screen and the field of view of the images, so as to blur the phosphor screen mottle.

Another embodiment of the invention concerns a method and a system for capturing multimodal images of an object. The method may include steps and the system may include elements for placing the object in an immobilized state on an object stage; positioning a phosphor screen in an image path from the object to transduce ionizing radiation passing from the object to visible light; capturing a series of images of the object using the visible light; moving the phosphor screen incrementally to facilitate reduction of phosphor screen mottle in the series; removing the phosphor screen from the image path; and capturing at least one optical image of the object.

Yet another embodiment of the invention concerns a method and a system for capturing an individual image of the immobilized object by the use of the phosphor screen, wherein the phosphor screen is incrementally displaced during the acquisition through a distance larger than the phosphor grain size and smaller than the difference between the physical size of the phosphor screen and the field of view of the image, and wherein the ionizing radiation is switched off during each incremental displacement and switched on after each incremental displacement, so as to blur the phosphor screen mottle without blurring the image.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 8A shows a diagrammatic side view of the sample object stage of FIG. 6 wherein the phosphor screen is positioned for imaging MODE 1.

FIG. 8B shows a diagrammatic side view of the sample object stage of FIG. 6 wherein the phosphor screen is positioned for imaging MODE 2.

FIG. 14A is a blow-up showing section H of the image evaluation insert of the image shown in FIG. 13A.

FIG. 14B is a blow-up showing section H of the image evaluation insert of the image average shown in FIG. 13B.

FIG. 14C is a blow-up showing section H of the image evaluation insert of the image average shown in FIG. 13C.

DETAILED DESCRIPTION OF THE INVENTION

Figure 1:
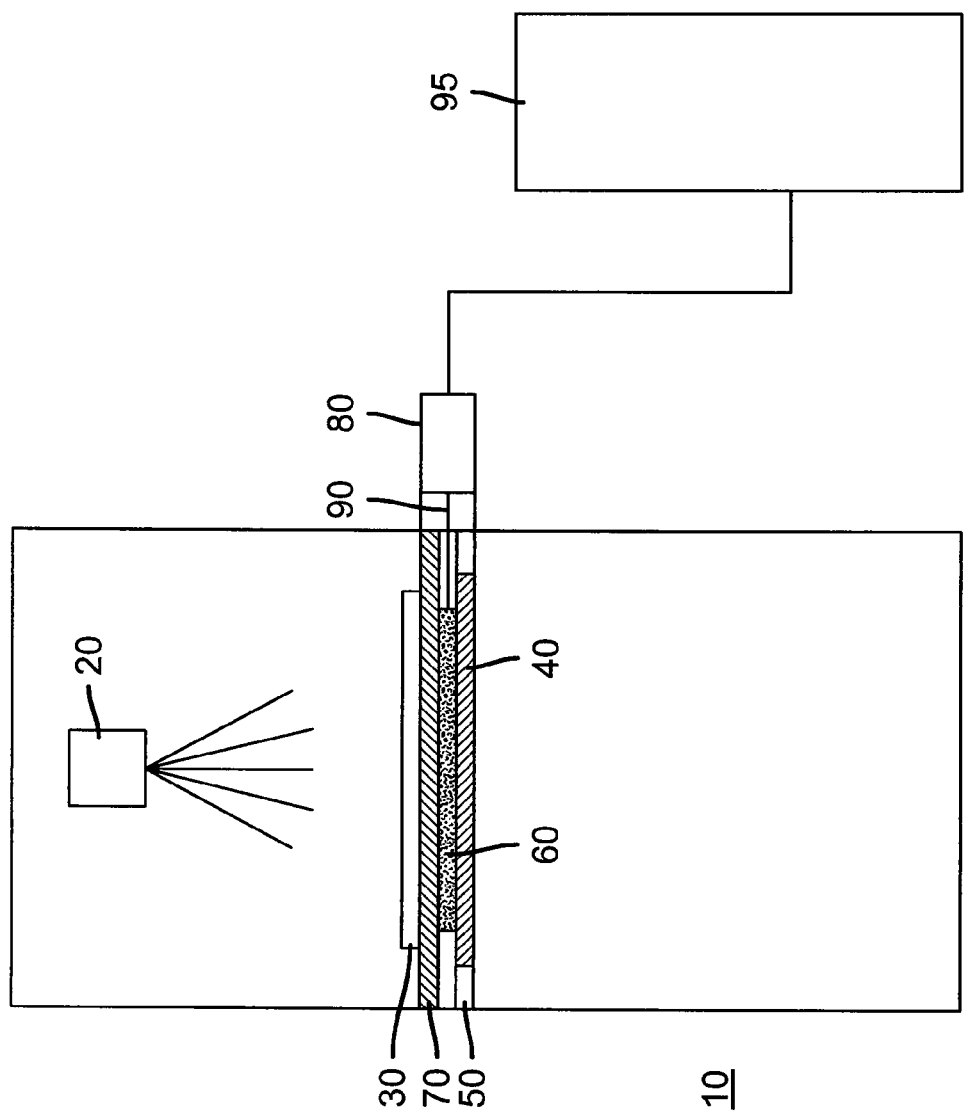
FIG. 1 shows a diagrammatic side view of a film-based radiographic or autoradiographic imaging system.

The following is a detailed description of the preferred embodiments of the invention, reference being made to the drawings in which the same reference numerals identify the same elements of structure in each of the several figures.

FIG. 1 illustrates a film-based radiographic or autoradiographic imaging system 10 comprising an X-ray source 20, used only for radiography, positioned opposite a sample object stage 30. A radiography or autoradiography film cassette 40 is located on the opposite side of stage 30 from source 20 in a film compartment 50. A phosphor screen 60 is located between stage 30 and cassette 40. A support frame 70 locates and supports stage 30, screen 60 and cassette 40. A linear motion device 80 is operatively connected to screen 60 by a connecting rod 90. A computer control system 95 is provided to control device 80 and X-ray source 20, when the source is activated for radiographic imaging and deactivated for autoradiographic imaging. During radiographic imaging, source 20 may be turned on and off by system 95 as needed during or following capture of an individual image or series of images.

Figure 2:
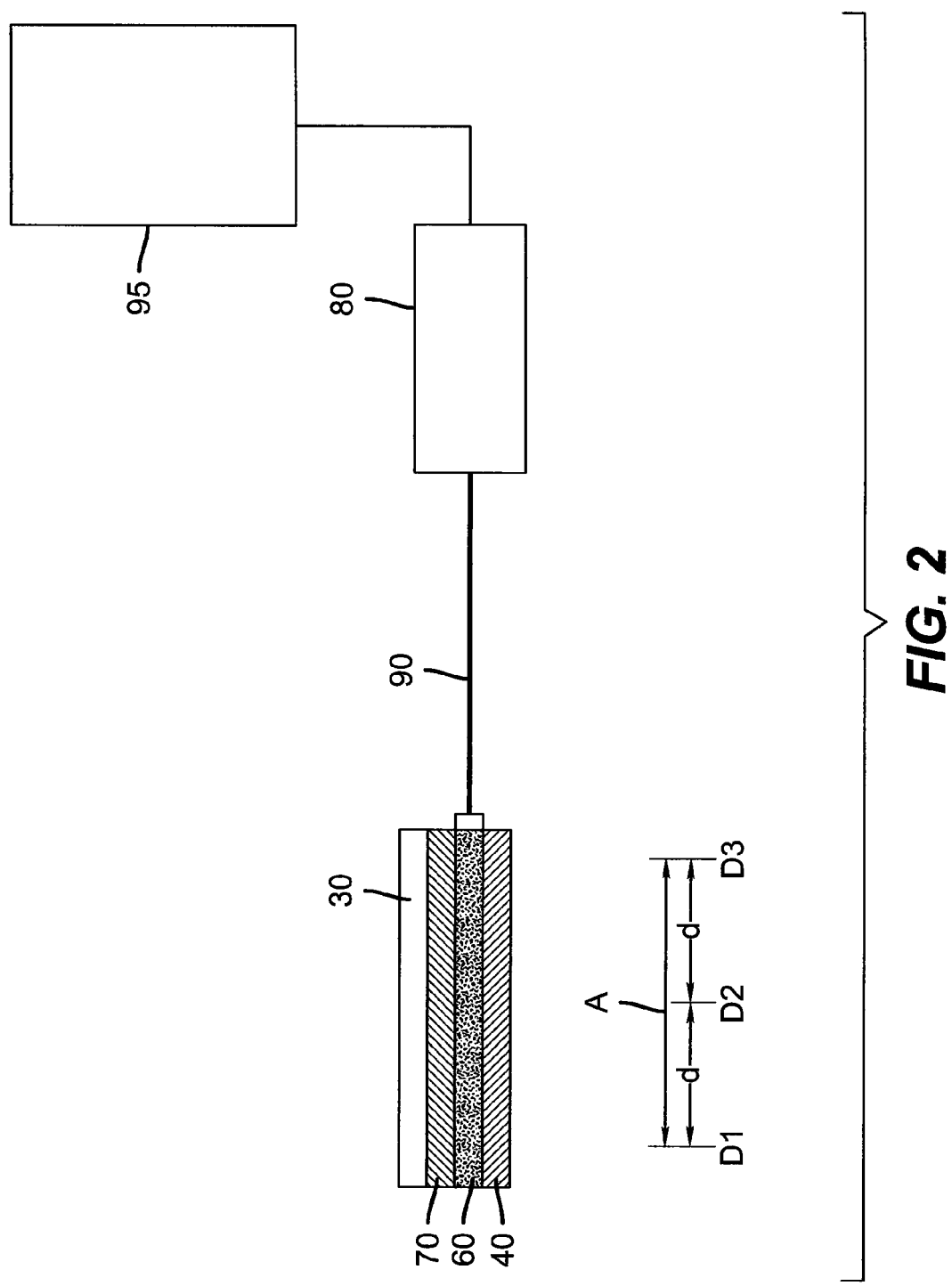
FIG. 2 shows a diagrammatic side view of a sample object stage and the phosphor screen of the film-based radiographic or autoradiographic imaging system of FIG. 1.

Regarding one embodiment of imaging system 10, FIG. 2 shows a diagrammatic side view of sample object stage 30. As illustrated, phosphor screen 60 is positioned beneath sample object stage 30. Film cassette 40 is positioned beneath screen 60, which is slideably mounted for motion in a plane parallel to sample object stage 30 and film cassette 40. Phosphor screen 60 is slideable in the direction of arrow A relative to frame 70 and in approximate contact with film cassette 40. Linear motion device 80 may be a linear induction motor connected to phosphor screen 60 via a connecting rod 90.

Figure 3:
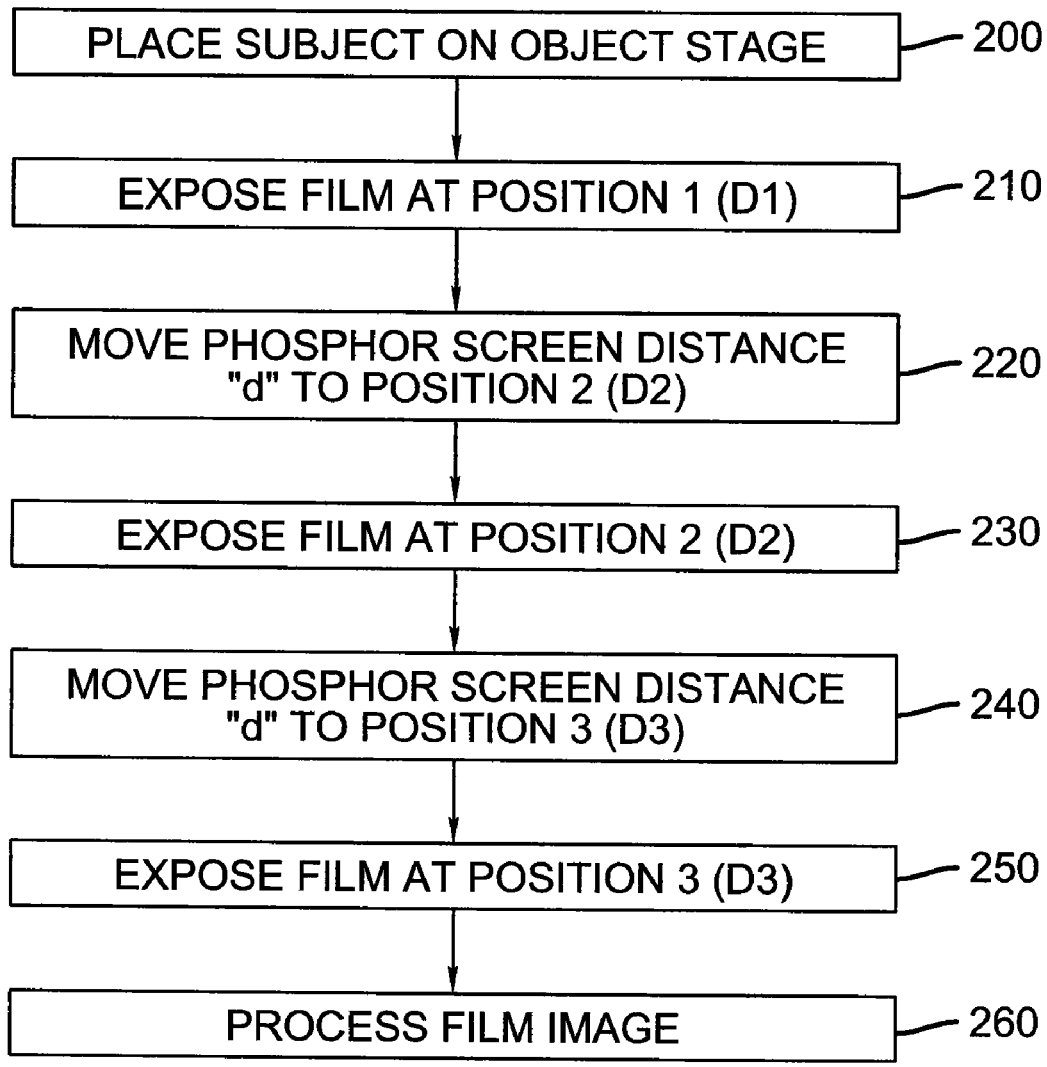
FIG. 3 shows a work flow diagram in accordance with a method of the present invention, in which film is used to capture images.

FIG. 3 illustrates an embodiment of a method performed by imaging system 10 in accordance with the invention. A subject such as a mouse in an immobilized state (not shown) is placed on object stage 30 in step 200. A series of individual images of the subject is acquired using phosphor screen 60 in steps 210, 230 and 250. Image capture may be achieved (i) with a single film that is multiply exposed at different incremental positions of screen 60 or (ii) with multiple films exposed in series at different incremental positions of screen 60. In the first instance, after each of the series of separate images is captured on the film in cassette 40, source 20 is turned off and phosphor screen 60 is displaced by device 80 by a distance "d" in steps 220 and 240, so as to facilitate reduction of phosphor screen mottle. This distance "d" is larger than the phosphor grain size (typically between 1 and 20 µm) but smaller than the difference between the physical size of the phosphor screen 60 and the field of view of each image on the film in cassette 40. The position of screen 60 for each image is indicated by D1, D2, D3 . . . Dn in FIG. 4. The time between each image taken at D1, D2, D3 . . . Dn, while source 20 is off, should exceed the time required for the phosphorescence to decay to a sufficiently low level (e.g., 1% after 1.5 sec for terbium-doped gadolinium oxysulfide) to achieve a desired dynamic range. The effect of the displacement of the phosphor screen between images results in the blurring of the phosphor screen mottle when the multiply-exposed film is processed in step 260. In the second instance, separate films are used for each image of the series; but otherwise, the process is the same. Alternatively, in either instance, the phosphor screen may be moved during the capture of an individual image, and the source 20 may be turned off during movement of the screen. During autoradiographic imaging, the source of radiation is within the subject and cannot be turned on or off; so, a mechanical shutter, not illustrated, must be provided to prevent radiation from the subject from reaching the film while the phosphor screen is being moved.

Figure 4A:
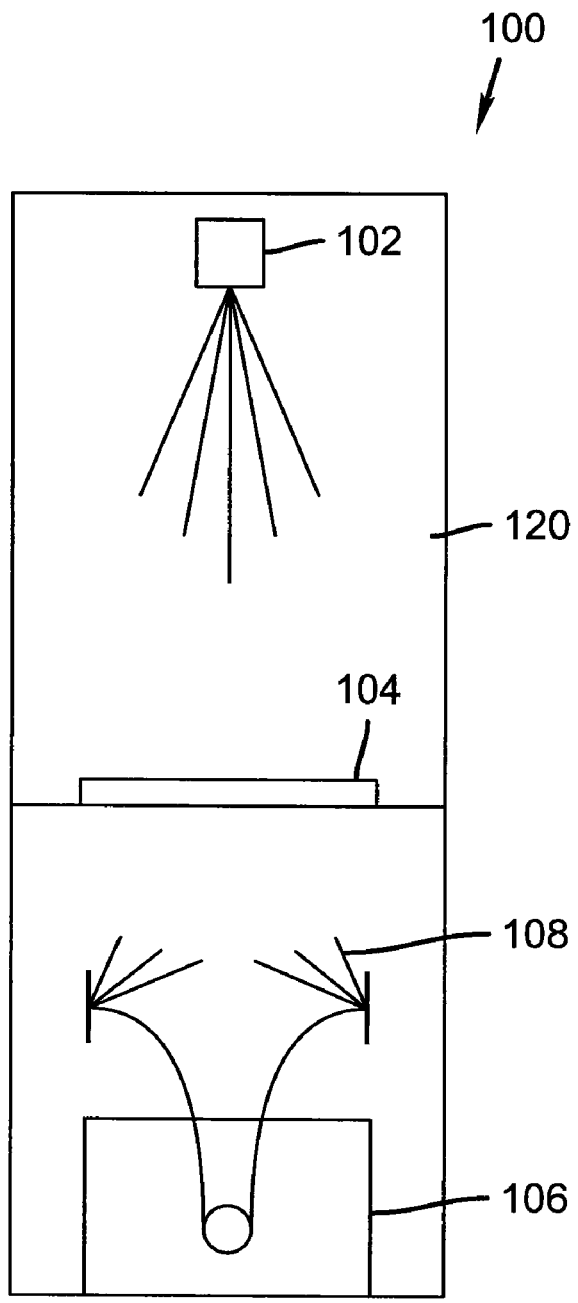
FIG. 4A shows a diagrammatic side view of a digital radiographic or autoradiographic imaging system in accordance with the present invention.
Figure 4B:
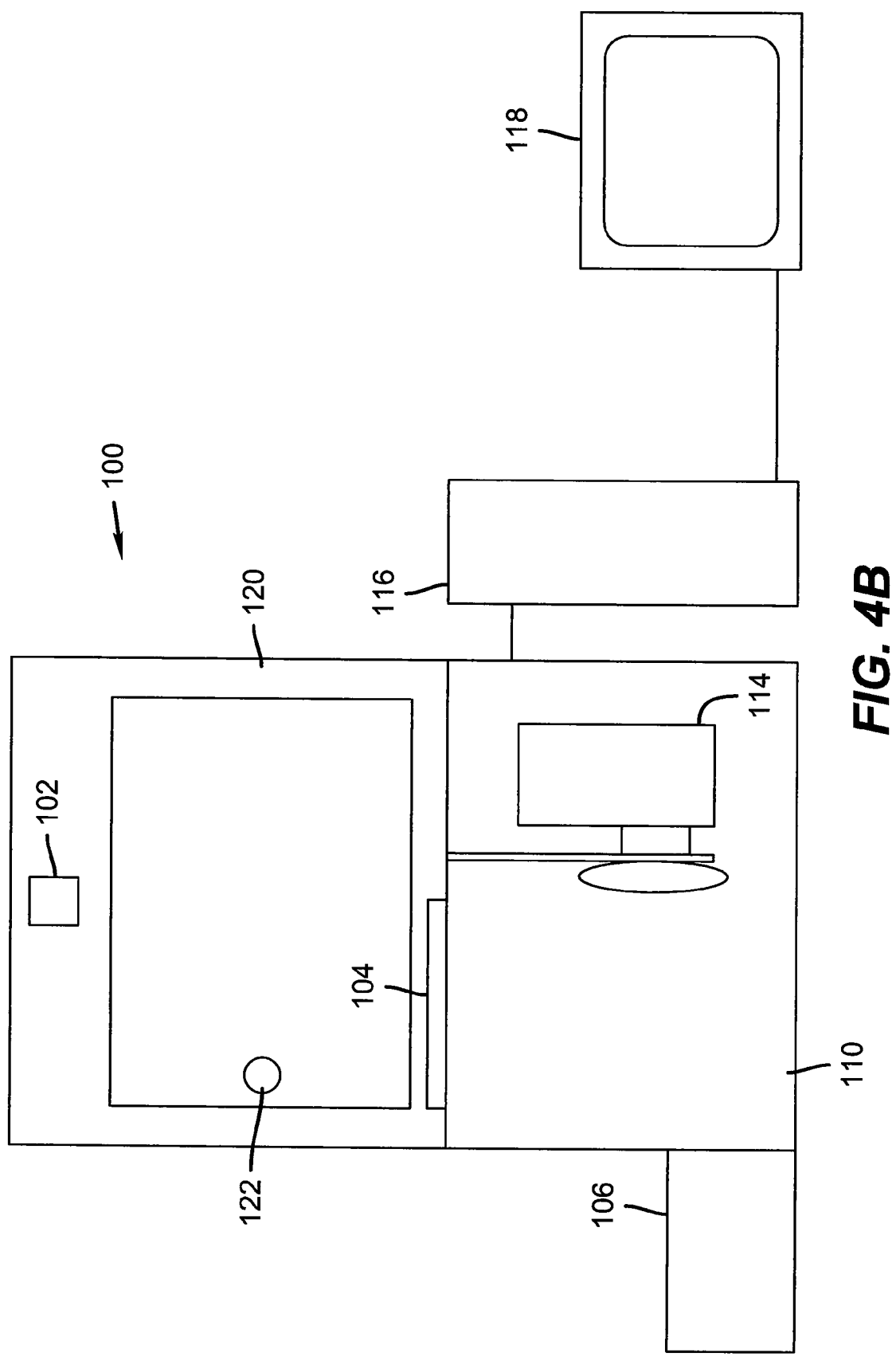
FIG. 4B shows a diagrammatic front view of the imaging system of FIG. 4A.
Figure 5:
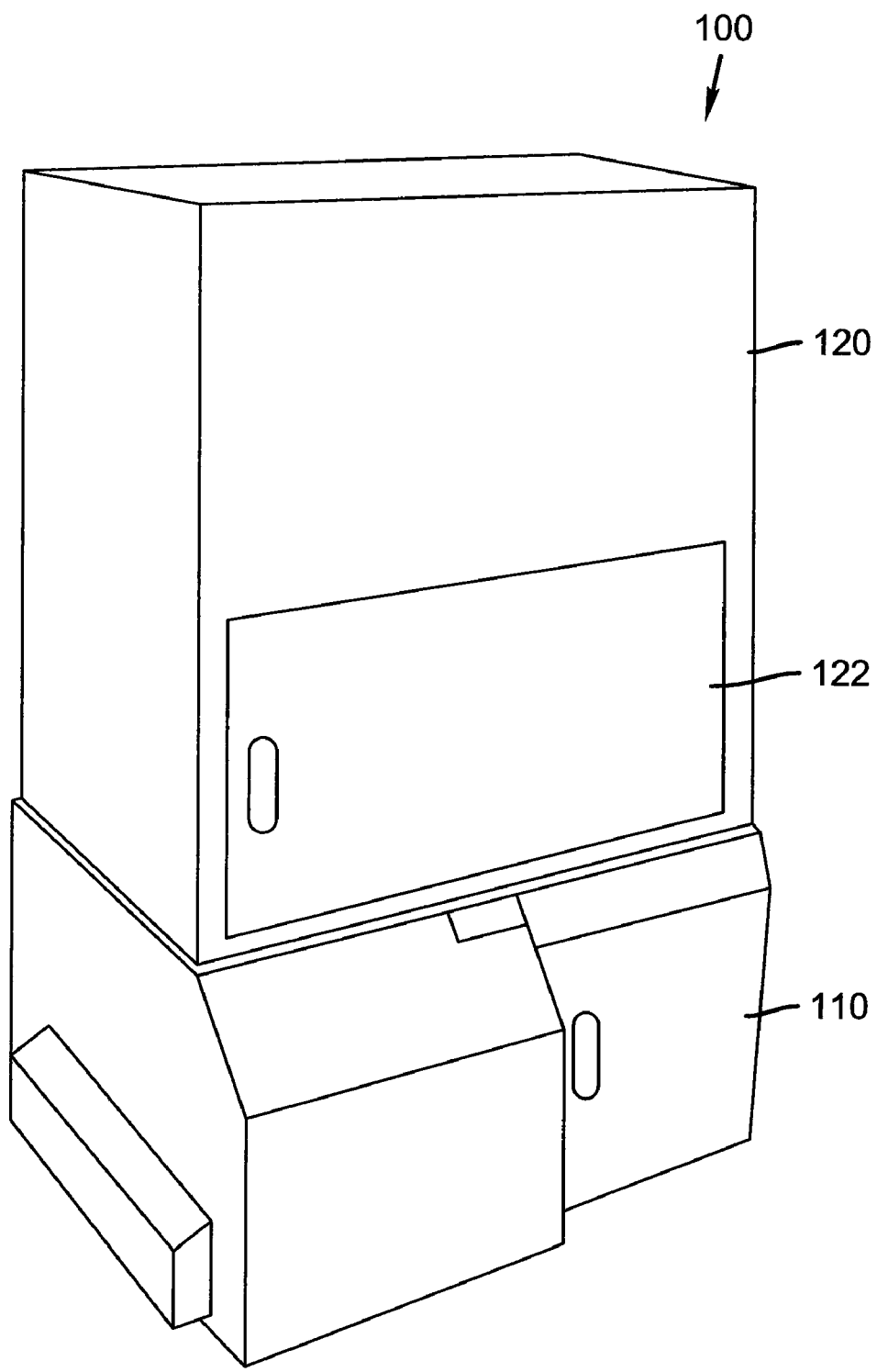
FIG. 5 shows a perspective view of the imaging system of FIGS. 4A and 4B.

FIGS. 4A, 4B and 5 show an electronic, digital radiographic or autoradiographic imaging system 100, used for high spatial resolution radiography or autoradiography, including an X-ray source 102 and a sample object stage 104. Imaging system 100 may be a multimodal type of imaging system such as a KODAK In-Vivo Imaging System FX Pro. This type of multimodal optical, radiographic and autoradiographic imaging system 100, in addition to the X-ray source 102, may have a programmable multispectral light source 106 with fiberoptic bundles 108 for illumination delivery, an optical compartment 110, a lens and camera system 114, and a communication/computer control system 116 with a display device 118, for example, a computer monitor. Such a multimodal imaging system is disclosed in the previously mentioned U.S. patent applications Ser. Nos. 11/221,530 of Vizard et al and 61/024,621 of Feke et al. Sample object stage 104 is disposed within a sample environment 120, which allows access to the object being imaged. Preferably, sample environment 120 is light-tight and fitted with light-locked gas ports for environmental control. Such environmental control might be desirable for controlled radiographic imaging or for support of particular specimens.

Imaging system 100 can include an access means or member 122 to provide convenient, safe and light-tight access to sample environment 120. Access means are well known to those skilled in the art and can include a door, opening, labyrinth, and the like. Additionally, sample environment 120 is preferably adapted to provide atmospheric control for sample maintenance or soft X-ray transmission (e.g., temperature/humidity/alternative gases and the like). Environmental control enables practical radiographic contrast below 8 KeV (air absorption) and aids in life support for biological specimens.

Figure 6:
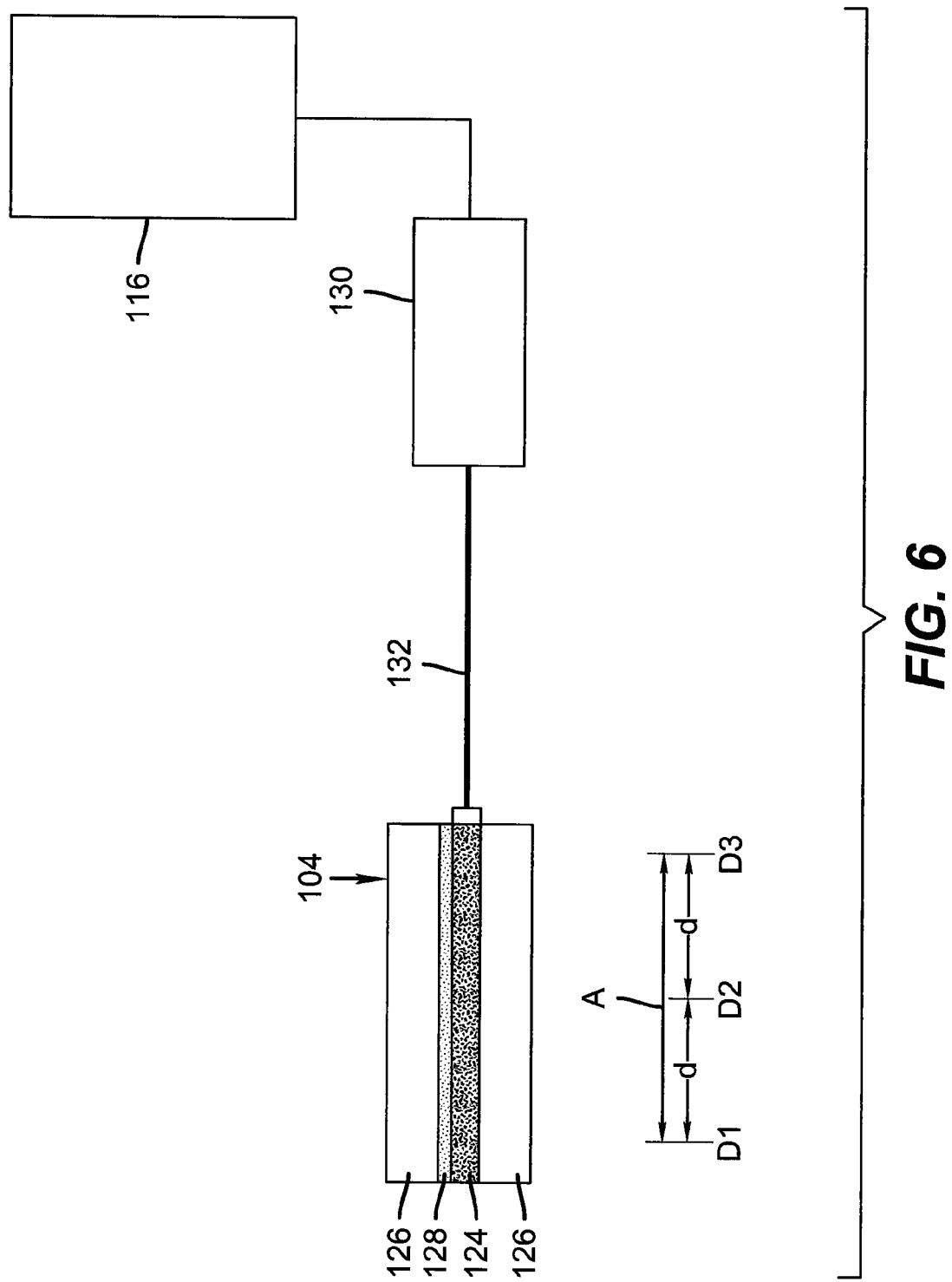
FIG. 6 shows a diagrammatic side view of the sample object stage of digital radiographic or autoradiographic imaging system of FIGS. 4A, 4B and 5.

FIG. 6 illustrates an embodiment of digital imaging system 100 of FIGS. 4A, 4B and 5. A phosphor screen or plate 124 is slideably mounted for motion in a plane parallel to sample object stage 104. Stage 104 includes a rectangular frame 126 to support and stretch a thin plastic support sheet 128 selected so as to support the weight of a sample. Sheet 128 is optically clear and free of significant interfering fluorescence.

While those skilled in the art might recognize other configurations, in one embodiment, phosphor screen 124 is mounted for translation in the direction of arrow A relative to frame 126, in intimate contact with support sheet 128 supporting an object to be imaged. A linear motion device 130 such as a linear induction motor is connected to phosphor screen 124 via a connecting rod 132 and controlled by system 116.

Figure 7:
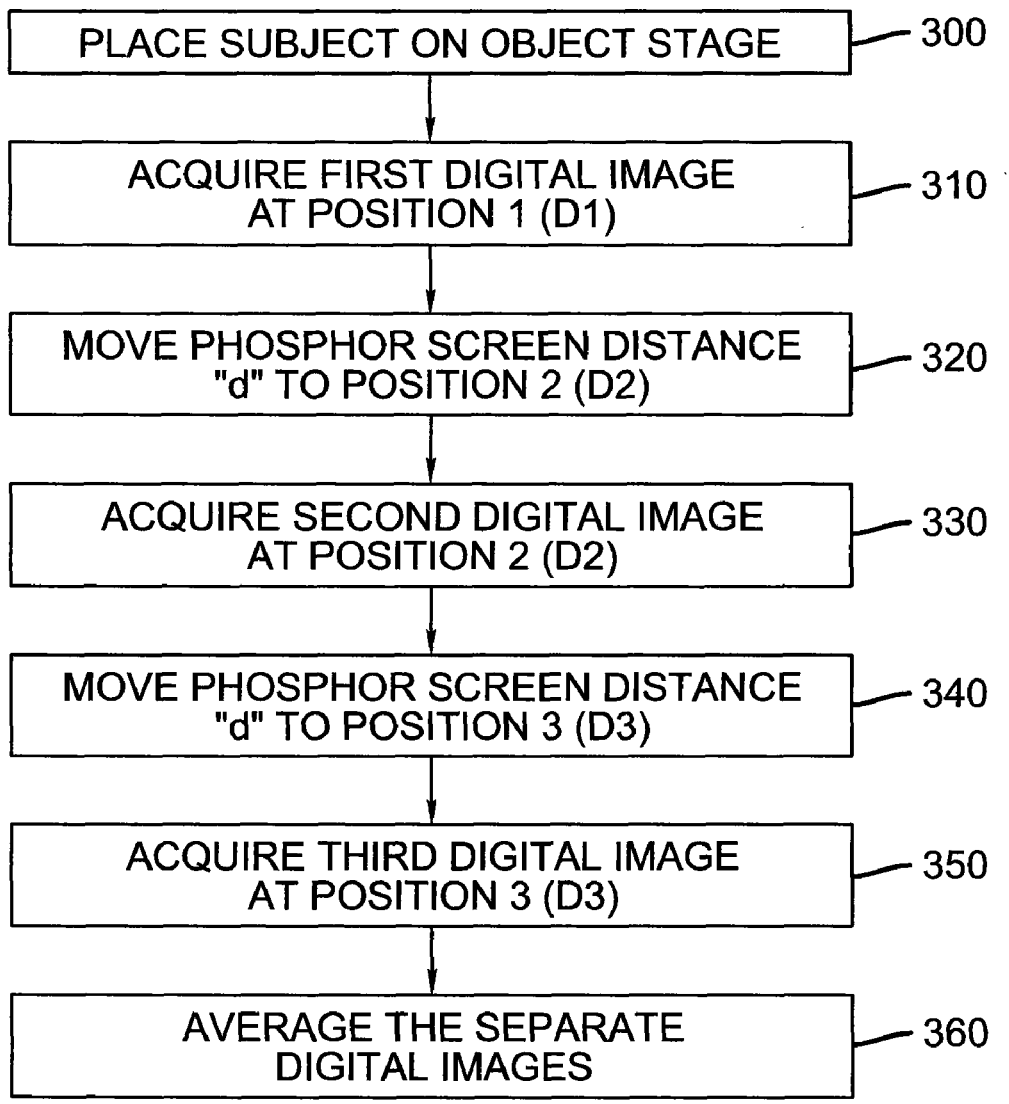
FIG. 7 shows a work flow diagram in accordance with a method of the present invention in which a digital camera is used to capture images.

FIG. 7 illustrates an embodiment of a method performed by system 100. A subject such as a mouse in an immobilized state (not shown) is placed on object stage 104 in step 300. A series of individual radiographic images of the subject is acquired using phosphor screen 124 in steps 310, 330 and 350. Source 102 may be turned off between images or left on from image to image. During autoradiographic imaging, the source of radiation is within the subject and cannot be turned on or off; so, an electrical or mechanical shutter in lens and camera system 114, not illustrated, must be used to prevent radiation from the subject from reaching the sensor of the camera while the phosphor screen is being moved. As the series of separate images is captured via camera system 114, between image captures phosphor screen 124 is displaced by device 130 by a small distance "d" in steps 320 and 340. This distance "d" is larger than the phosphor grain size but smaller than the difference between the physical size of the phosphor screen 124 and the field of view of the images. The position of screen 124 for each image is indicated by D1, D2, D3 . . . Dn in FIG. 6. When source 102 is turned off between radiographic images or the camera shutter is closed between autoradiographic images, the time between each image taken at D1, D2, D3 . . . Dn should exceed the time required for the phosphorescence to decay to a sufficiently low level (e.g., 1% after 1.5 sec for terbium-doped gadolinium oxysulfide) to achieve a desired dynamic range. The resultant digital images are then pixelwise averaged mathematically, using techniques familiar to those skilled in the art of digital image processing, so as to blur the phosphor screen mottle in step 360. Alternatively, the phosphor screen may be moved during the capture of an individual image, and the source 102 may be turned off during movement of the screen.

Considering the modes of operation of system 10 and system 100, the skilled person will understand that image capture may occur during an interval when the film or digital camera or other imaging device captures light from the phosphor screen under (i) on-off control of the camera or imaging device or (ii) on-off control of X-ray source 102. The skilled person further will understand that image capture could be controlled by a combination of camera and X-ray source control.

In another embodiment of the method of the invention, the digital radiographic or autoradiographic imaging system 100 of FIGS. 4A, 4B and 5 is used in the multimodal imaging system mode. In that mode, imaging system 100 is capable of analytical imaging of objects such as small mammals, insects, fish, seeds, biopsies in differing modes, including bright-field, dark-field (e.g., luminescence and fluorescence), and radiographic or autoradiographic modes.

Figure 9A:
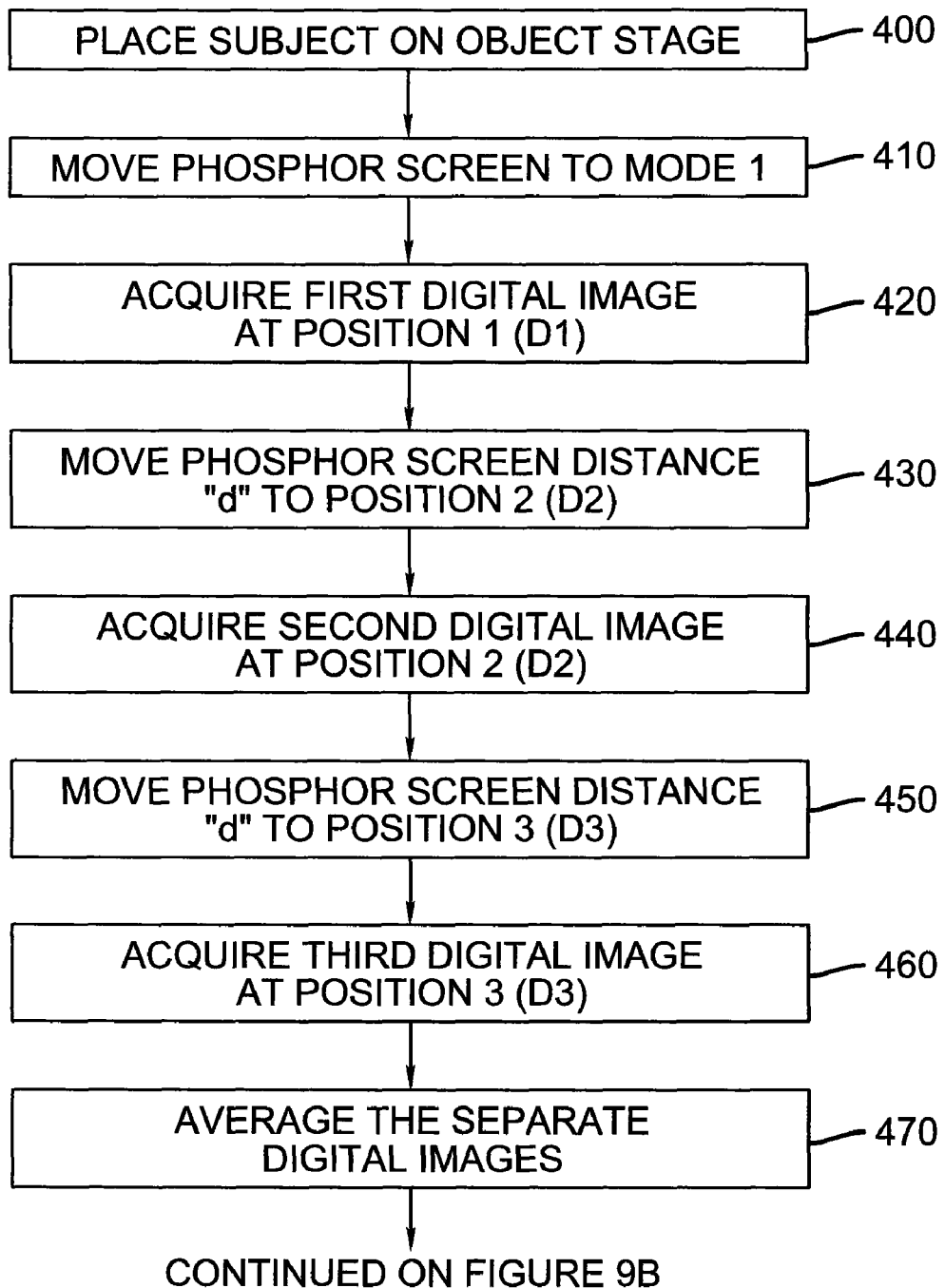
FIGS. 9A and 9B show a work flow diagram in accordance with a method of the present invention in which a digital camera is used to capture images.
Figure 9B:
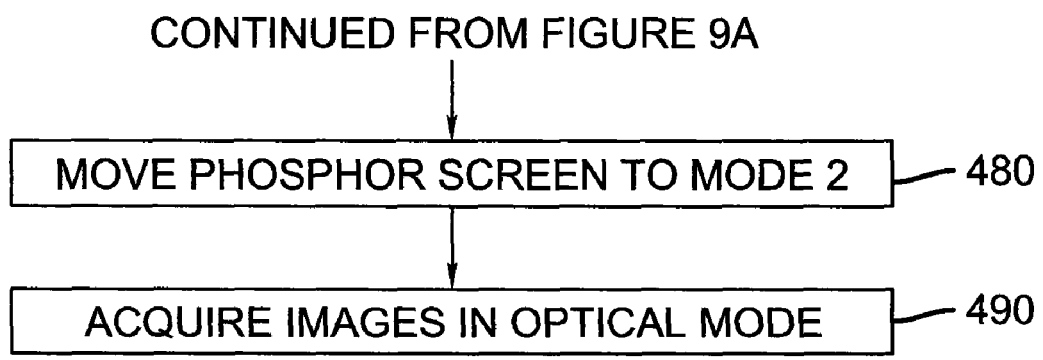

In use of the multimodal imaging mode described in the previously mentioned U.S. patent application Ser. No. 11/221,530 of Vizard et al and corresponding U.S. Publication 2006/0064000, a method of the invention is illustrated in FIGS. 8A, 8B and the workflow of FIGS. 9A and 9B. The immobilized subject (mouse) in positioned on object stage 104 in step 400. Phosphor screen 124 is moved by device 130 into position for digital radiographic or autoradiographic imaging MODE 1 in step 410, where it is in an overlapping, proximate arrangement with sample object stage 104. A series of individual images of the subject is acquired in steps 420, 440 and 460. As the series of separate images is captured via camera system 114, phosphor screen 124 is displaced by a distance "d" by device 130 in steps 430 and 450. Distance "d" is larger than the phosphor grain size but smaller than the difference between the physical size of the phosphor screen 124 and the field of view of the images. Linear motion device 130 may be controlled by the communication and computer control system 116. The position for each image for example is indicated by D1, D2, D3 ... Dn in FIG. 6. The time between each image taken at D1, D2, D3 ... Dn should exceed the decay time of the phosphor material in the screen. The images are then averaged so as to blur the phosphor screen mottle in step 470. The phosphor screen 124 then is moved in step 480 out of the image path into position for optical imaging MODE 2 and optical images including bright-field and dark-field (e.g. luminescence and fluorescence) images are acquired in step 490.

Still another embodiment of the invention concerns a method for producing a high-resolution digital image from a sequence of low-resolution digital images using a super-resolution technique. For example, an immobilized object and camera may be incrementally displaced with respect to each other during capture of a sequence of low-resolution digital images and the phosphor screen may also be displaced, incoherently from the displacement of the object and camera, for each of the low-resolution digital images by a distance larger than the phosphor grain size and smaller than the difference between the physical size of the phosphor screen and the field of view of the images, so as to blur the phosphor screen mottle.

Figure 10:
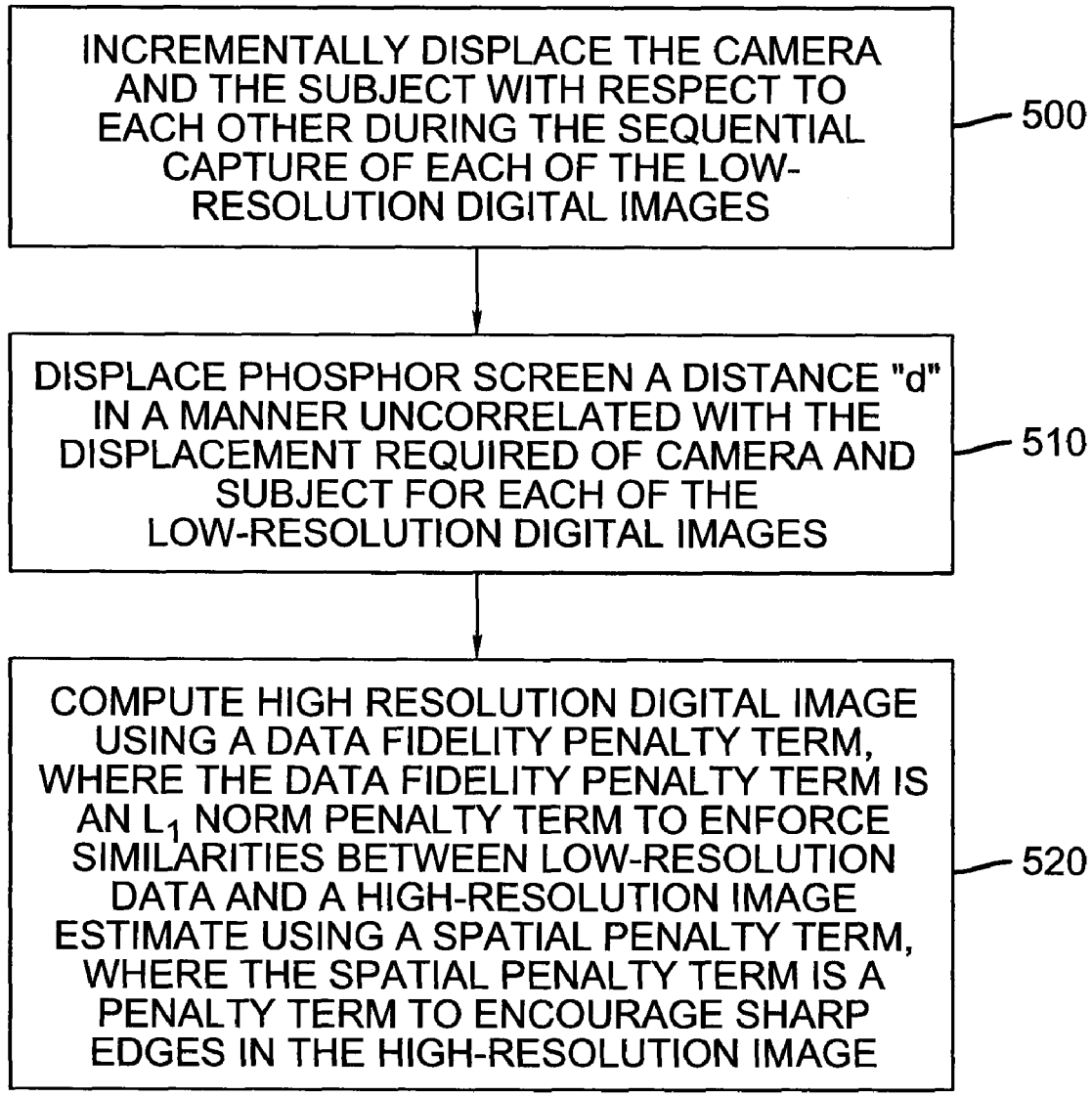
FIG. 10 shows a work flow diagram of another embodiment in accordance with a method of the present invention.
Figure 11:
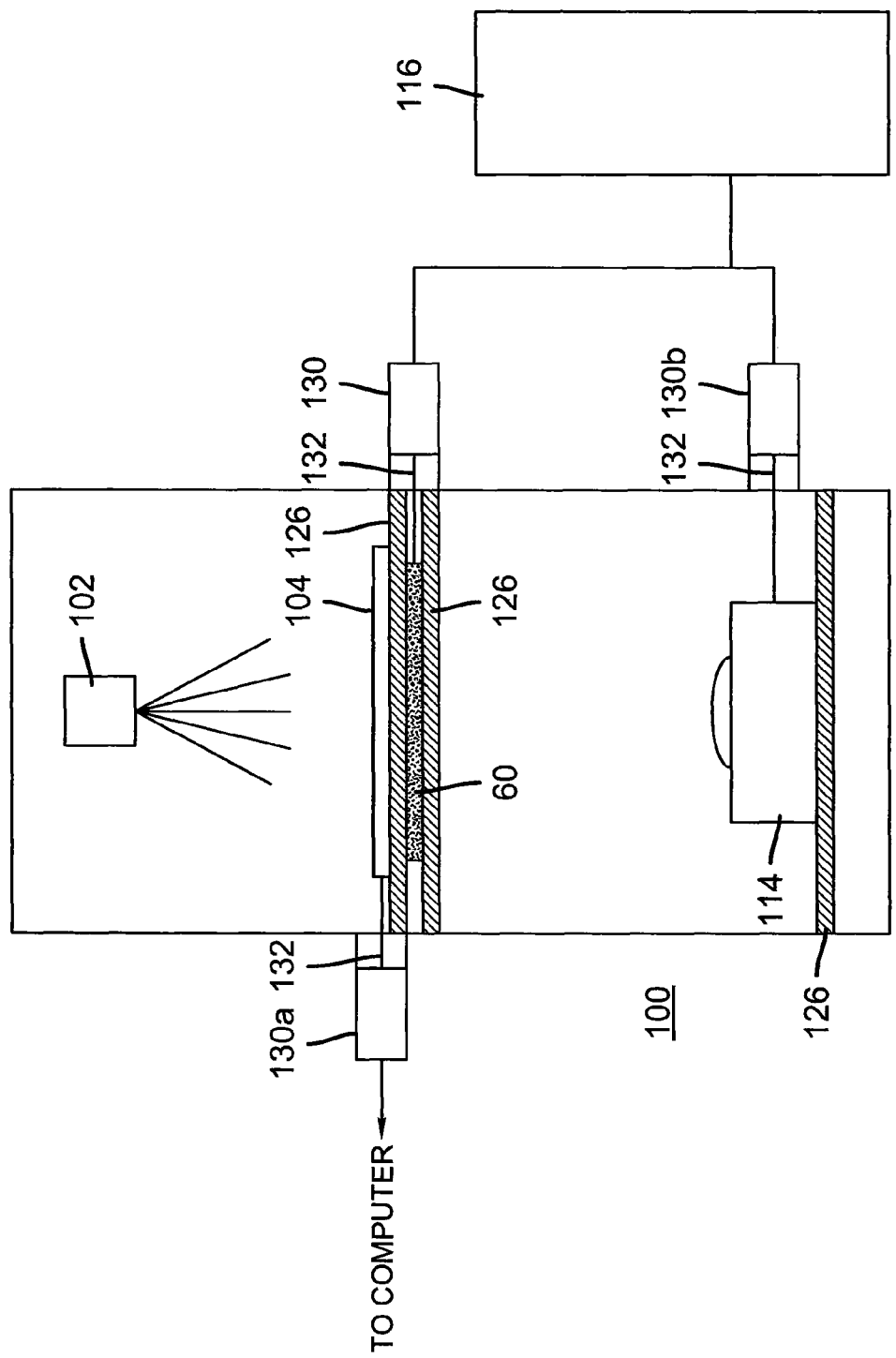
FIG. 11 shows a diagrammatic side view of another embodiment of the sample object stage and the phosphor screen of the digital radiographic or autoradiographic imaging system of FIGS. 4A and 4B.

For such a super-resolution embodiment, the workflow shown in FIG. 10 describes a method of obtaining a high resolution radiographic or autoradiographic image with reduced or eliminated screen mottle using the system illustrated in FIGS. 4A, 4B, and 11. A high-resolution digital image is computed from a sequence of low-resolution digital images using a super-resolution technique. Such a super-resolution technique is disclosed in detail in previously mentioned U.S. Patent Application Publication No. 2007/0217713, the disclosure of which is incorporated by reference into this specification. For example, the immobilized object on sample object stage 104 and camera 114 are incrementally displaced with respect to each other via linear motion devices 130a and 130b controlled by the computer 116 during capture of the sequence of low-resolution digital images in step 500. At the same time, phosphor screen 124 is also displaced via linear motion device 130 controlled by the computer 116 by the distance "d", larger than the phosphor grain size and smaller than the difference between the physical size of the phosphor screen 124 and the field of view of the images. Phosphor screen 124 is displaced in a manner uncorrelated with the displacement of camera 114 and object stage 104, for each of the low-resolution digital images, so as to blur the phosphor screen mottle in step 510. A high-resolution digital image is then computed in step 520 in accordance with the published application by using a data fidelity penalty term, where the data fidelity penalty term is an $L_1$ norm penalty term to enforce similarities between low-resolution data and a high-resolution image estimate using a spatial penalty term, where the spatial penalty term is a penalty term to encourage sharp edges in the high-resolution image.

Figure 12:
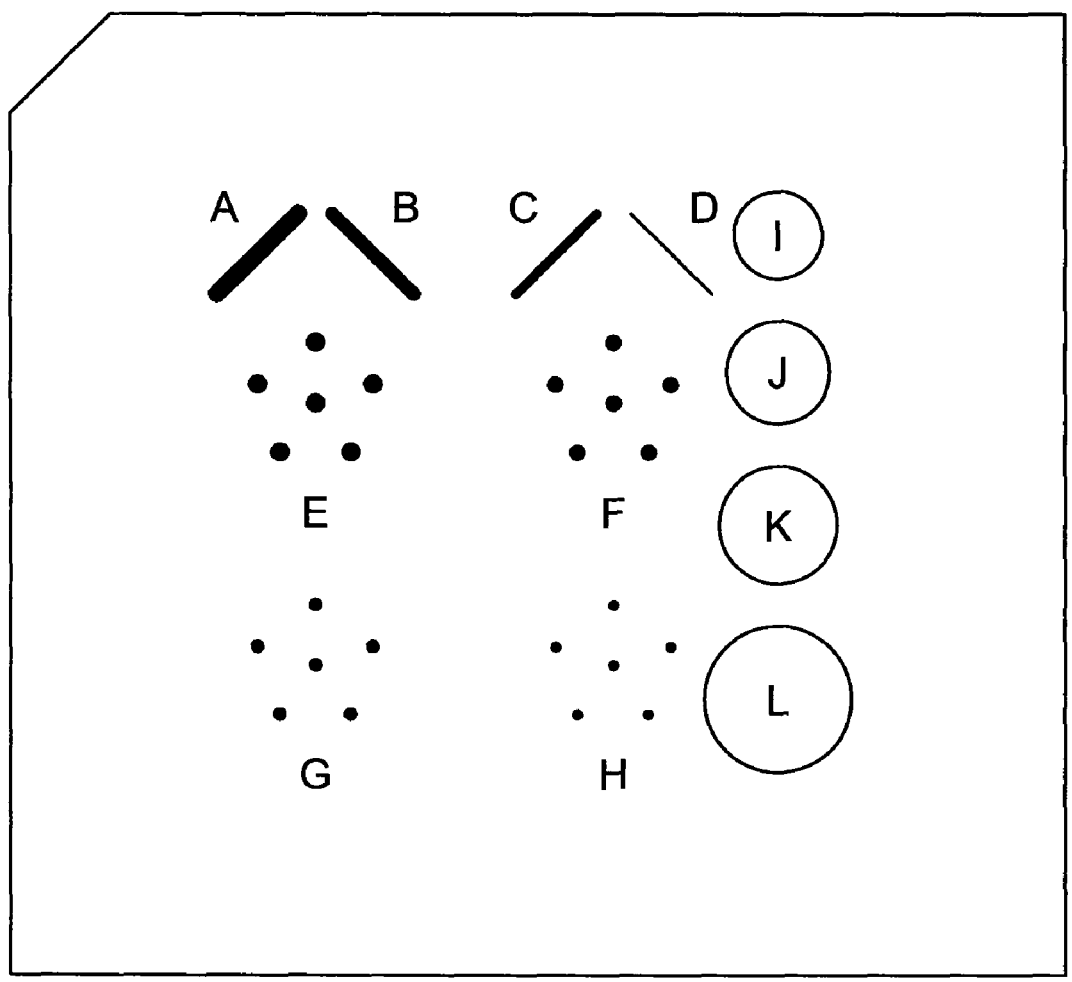
FIG. 12 is a diagrammatic view of an image evaluation insert of a digital stereotactic breast biopsy accreditation phantom.

Experimental Results:

FIG. 12 is a diagrammatic view of an image evaluation insert of a digital stereotactic breast biopsy accreditation phantom, such as Nuclear Associates Model 18-250. The insert is made of wax and contains test objects to simulate indications of breast cancer. Nylon fibers A, B, C and D of varying diameter simulate tissue fibrillar extensions in adipose tissue. Groups E, F, G and H of six alumina specks, wherein the diameter varies between groups, simulate punctuate calcifications. Lens-shaped masses I, J, K and L of varying thickness simulate tumor-like masses.

Figure 13A:
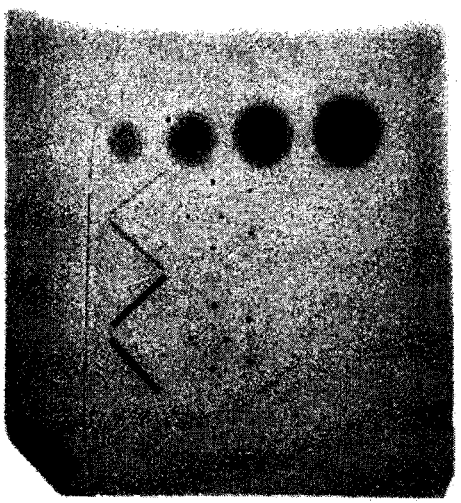
FIG. 13A is a single digital radiographic image of the image evaluation insert of FIG. 12 captured with a stationary phosphor screen for the sake of reference.
Figure 13B:
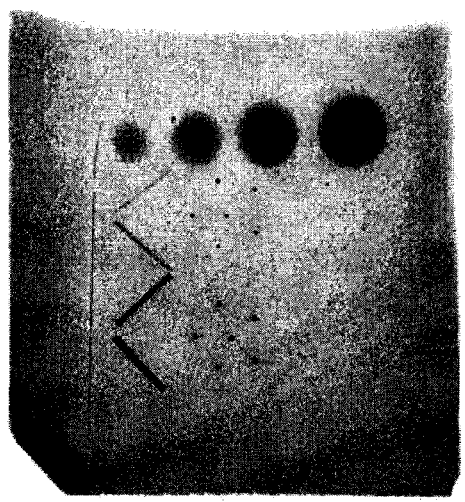
FIG. 13B is the image average of a plurality of (specifically sixteen) digital radiographic images of the image evaluation insert of FIG. 12 captured with a stationary phosphor screen for the sake of reference.
Figure 13C:
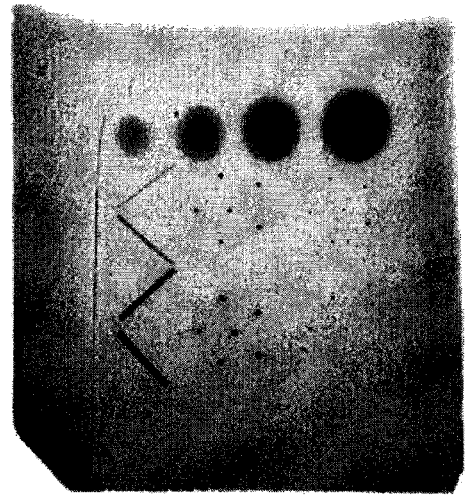
FIG. 13C is the image average of a plurality of (specifically sixteen) digital radiographic images of the image evaluation insert of FIG. 12 captured with an incrementally displaced phosphor screen using the system and method in accordance with the present invention.
Figure 15A:
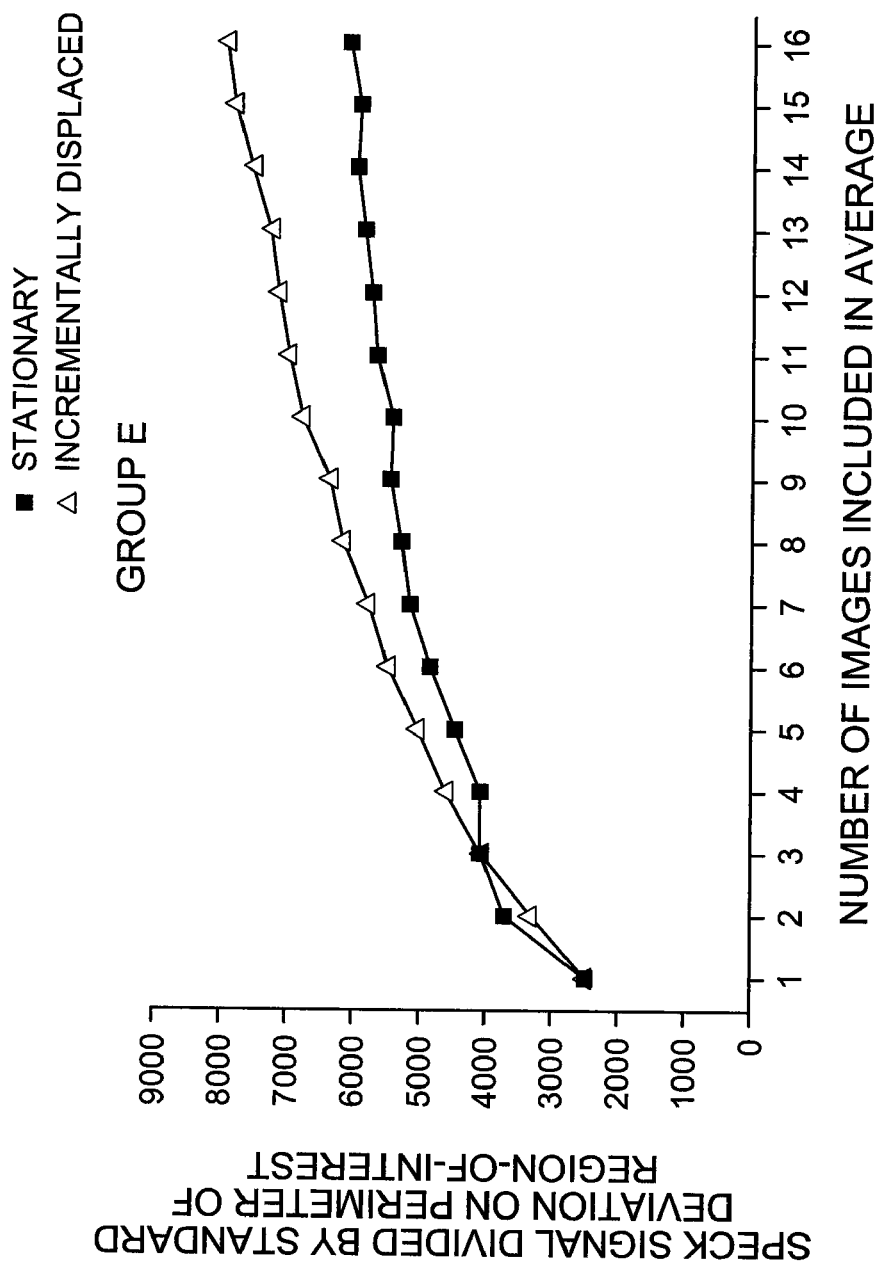
FIG. 15 is a graphical representation of the results of measurements of Groups E, F, G and H of the image evaluation insert of FIG. 12 acquired by the system and method in accordance with the present invention.
Figure 15B:
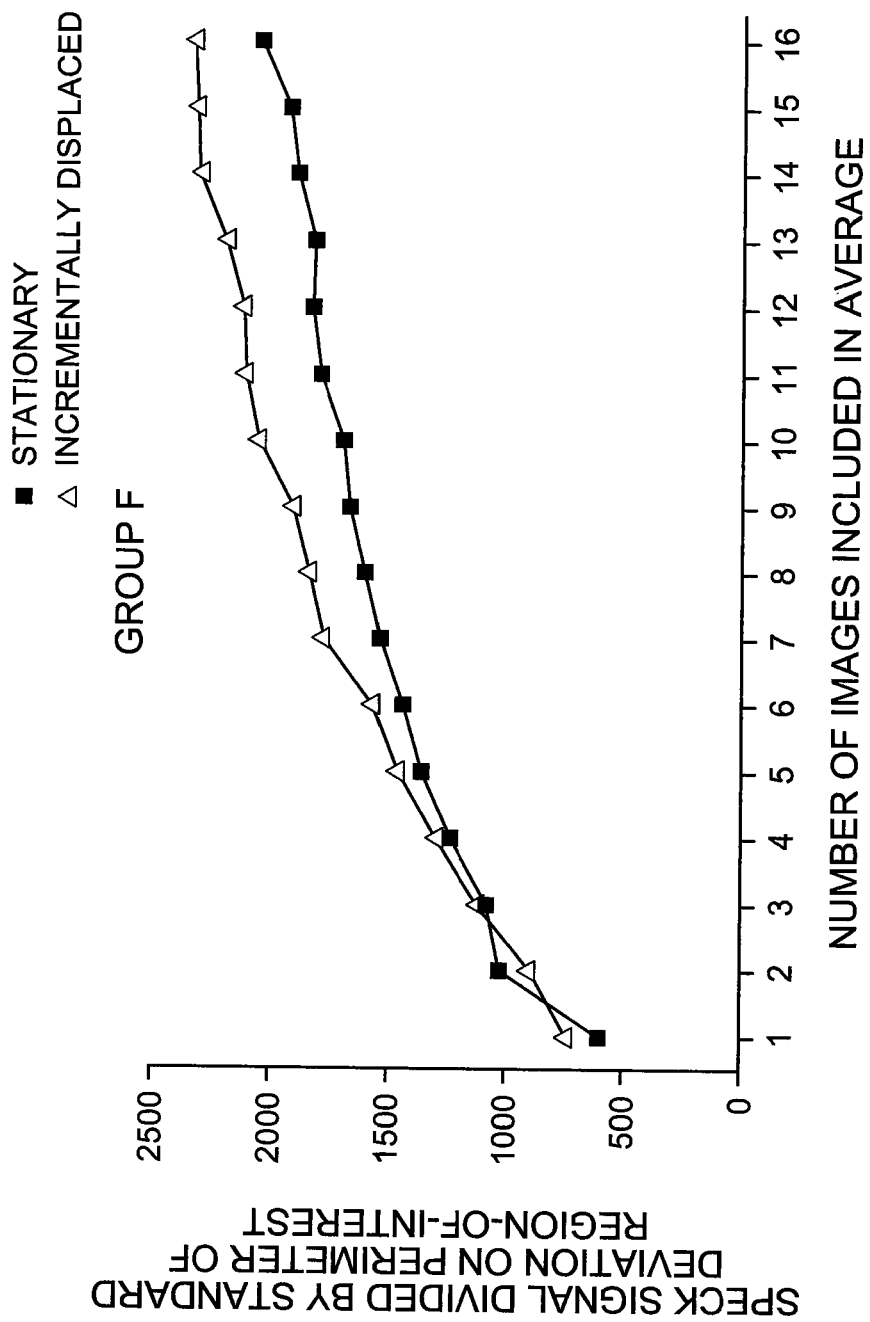
Figure 15C:
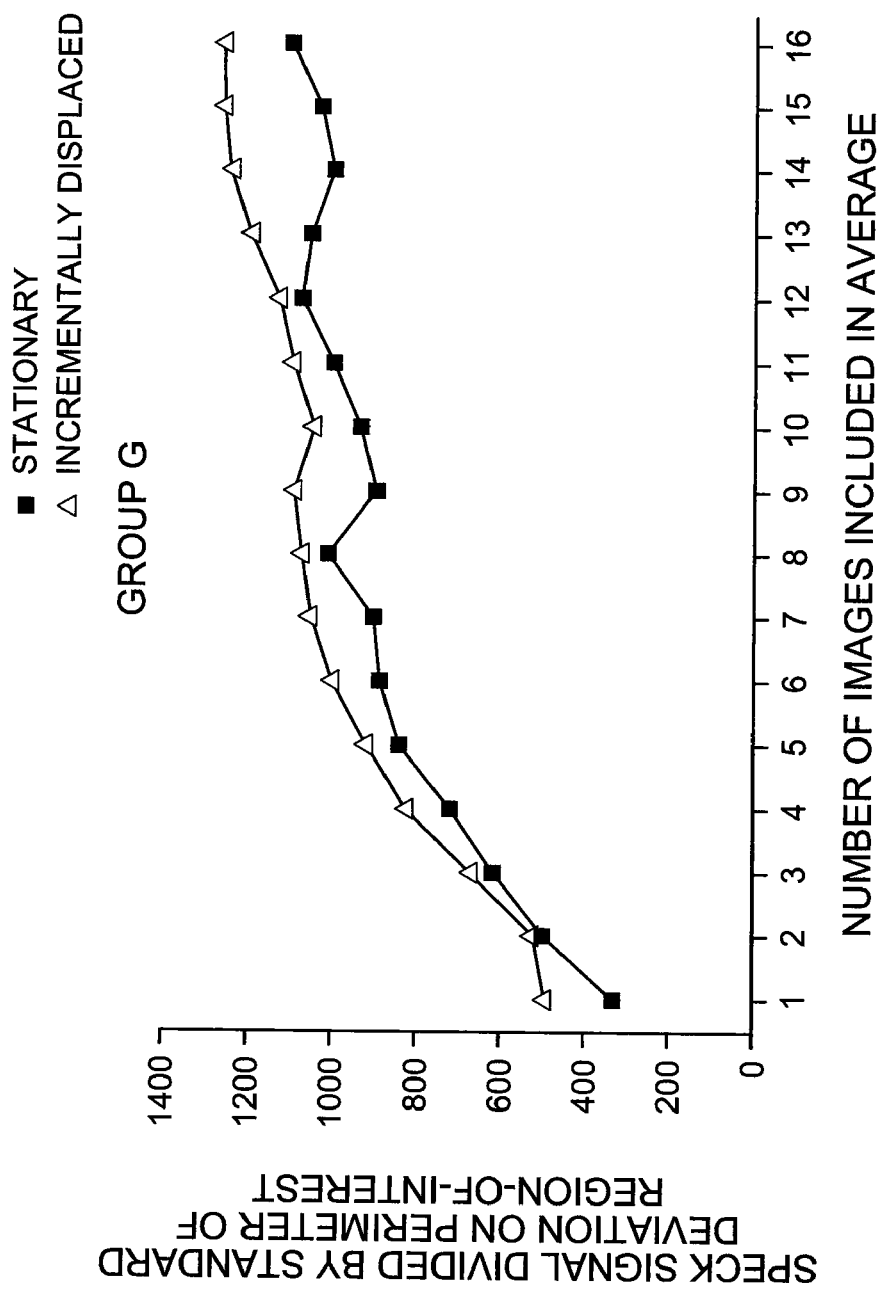
Figure 15D:
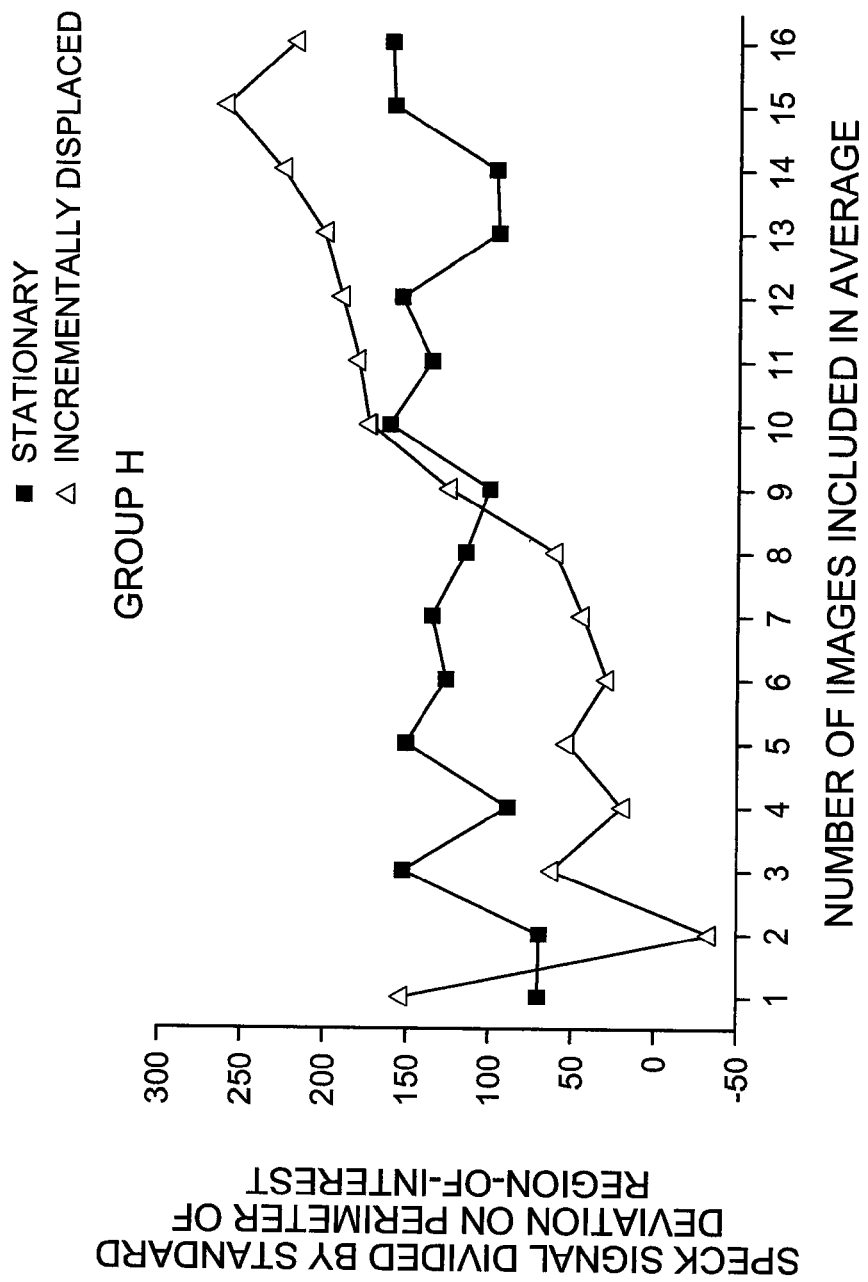

FIG. 13A is a single digital radiographic image of the image evaluation insert of FIG. 12 captured with a stationary phosphor screen for the sake of reference. FIG. 13B is the image average of a plurality of (specifically sixteen) digital radiographic images of the image evaluation insert of FIG. 12 captured with a stationary phosphor screen for the sake of reference. FIG. 13C is the image average of a plurality of (specifically sixteen) digital radiographic images of the image evaluation insert of FIG. 12 captured with an incrementally displaced phosphor screen using the system and method of FIGS. 4 to 7 in accordance with the present invention.

The alumina specks are well-suited to serve in the demonstration of the advantages of the present invention. Groups E, F, G, and H comprise alumina specks of diameter 0.54 mm, 0.32 mm, 0.24 mm, and 0.20 mm, respectively. FIG. 14A is a blow-up of image evaluation insert section H (see FIG. 12) of the image shown in FIG. 13A. Alumina specks 600 and phosphor screen defects 610 are visible. FIG. 14B is a blow-up of image evaluation insert section H of the image average shown in FIG. 13B. FIG. 14C is a blow-up of image evaluation insert section H of the image average shown in FIG. 13C. The comparison of FIGS. 14A,B, and C shows that the visual impact of the mottle in the background of the specks is reduced by averaging a plurality of images, and is reduced further by averaging a plurality of images wherein the phosphor screen is incrementally displaced compared to averaging a plurality of images wherein the phosphor screen is stationary. Furthermore, artifacts due to phosphor screen defects, such as those apparent in FIGS. 14A and B, are reduced by a great proportion by averaging a plurality of images wherein the phosphor screen is incrementally displaced.

FIG. 15 is a graphical representation of the results of measurements of the image evaluation insert of FIG. 12 acquired by the system and method of FIGS. 4 to 7 in accordance with the present invention. Graphs are shown for Groups E, F, G and H comparing a quantitative figure-of-merit for the detection of the specks plotted against the number of images included in the image average for each of the four sections of differently sized specks, for images captured with an incrementally displaced phosphor screen and a stationary phosphor screen. The figure-of-merit is the ratio of the signal, defined as the negative of the sum of the digital counts in each pixel within a region of interest around each speck after the median value of the digital counts in the pixels on the perimeter of the region of interest has been subtracted from the digital count value in each pixel within the region of interest, to the standard deviation of the digital counts in each pixel on the perimeter of the region of interest. The data show that the figure-of-merit generally increases (i.e., improves) with increasing number of images included in the image average, and furthermore that the figure-of-merit generally increases faster for the incrementally displaced phosphor screen compared to the stationary phosphor screen. For the case of the speck group in section H, which is comprised of the smallest specks, the data is so noisy that only the incrementally displaced phosphor screen exhibits a marked improvement in the figure-of-merit after a substantial number of images have been included in the image average.

Figure 16B:
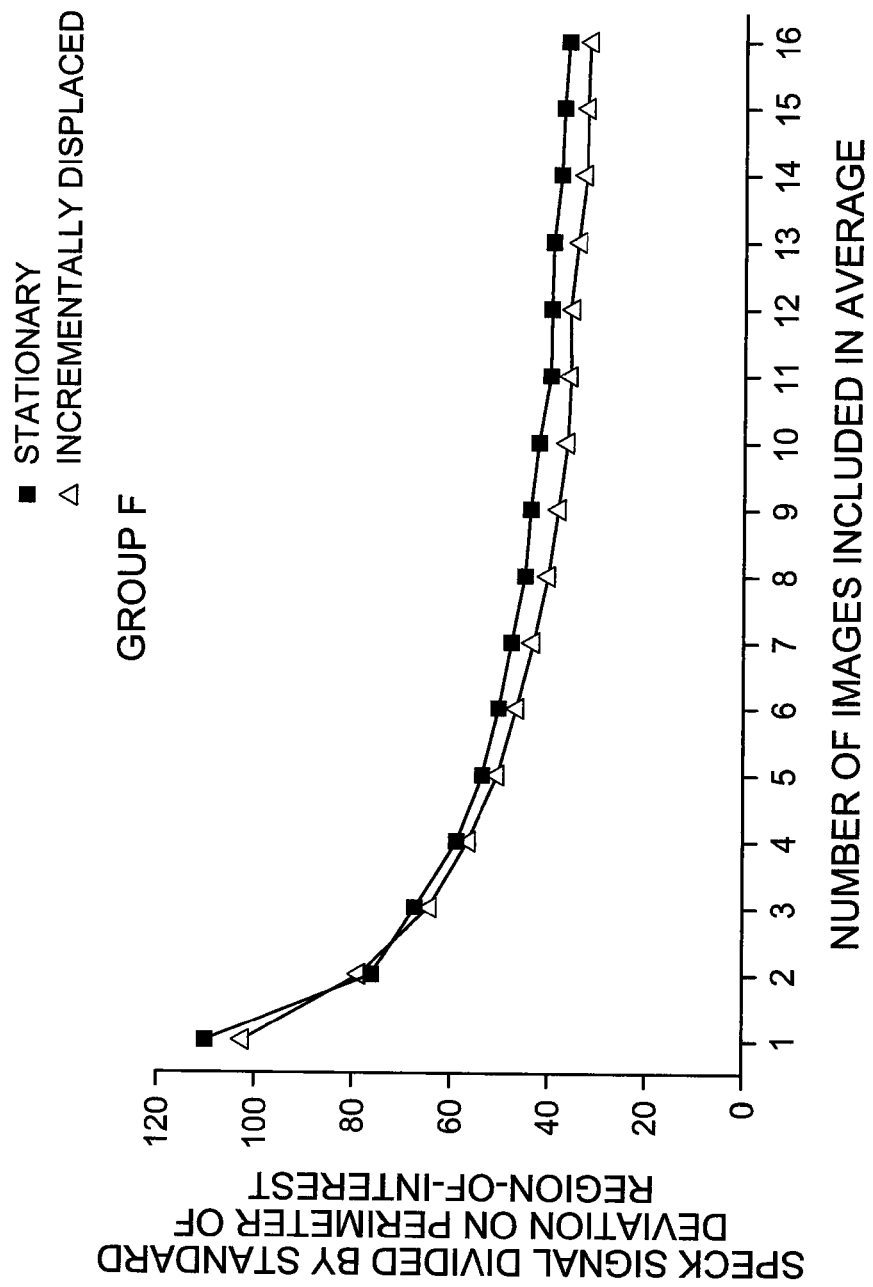
FIG. 16 is another graphical representation of the results of measurements of Groups E, F, G and H of the image evaluation insert of FIG. 12 acquired by the system and method in accordance with the present invention.
Figure 16C:
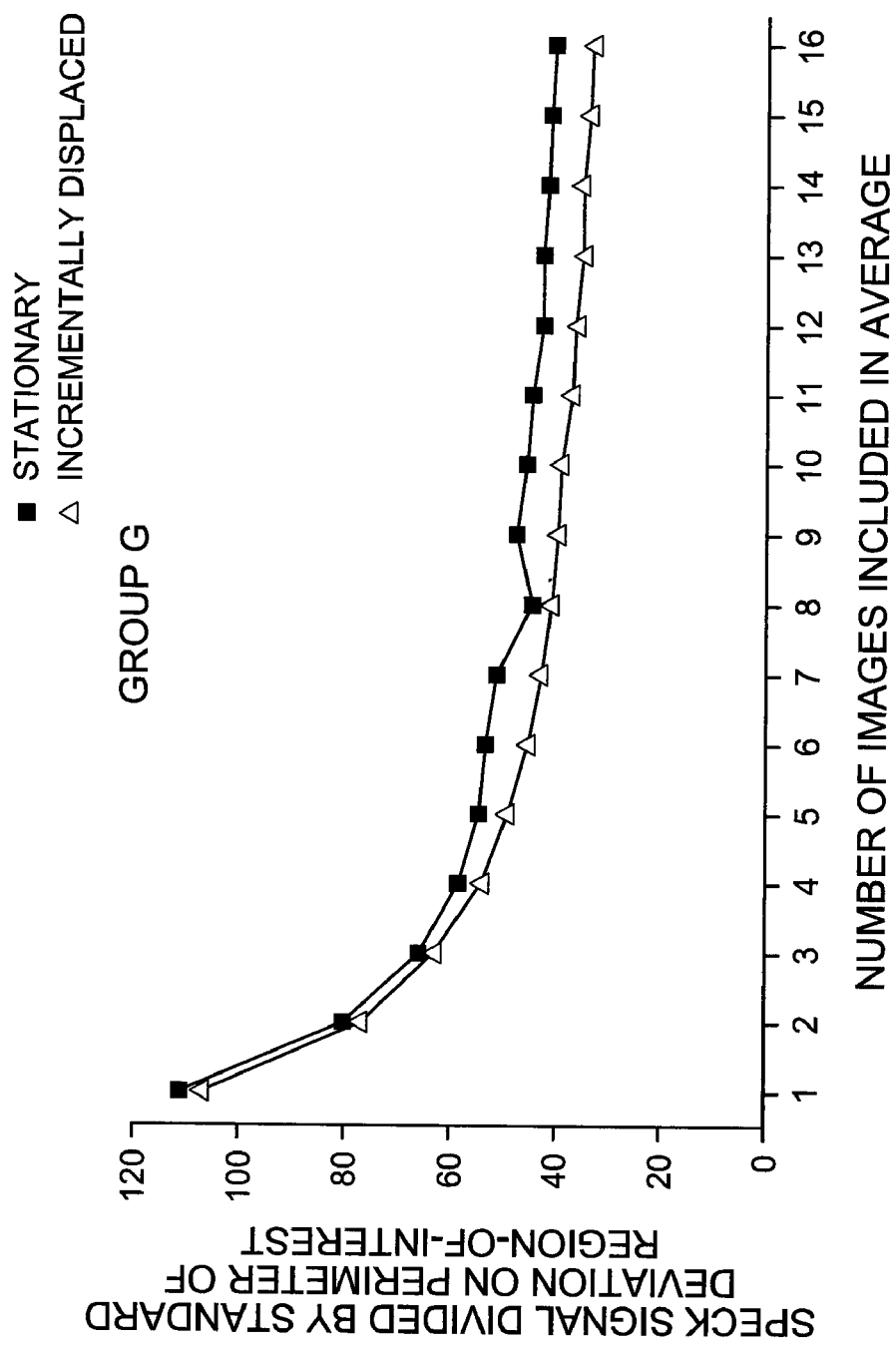
Figure 16D:
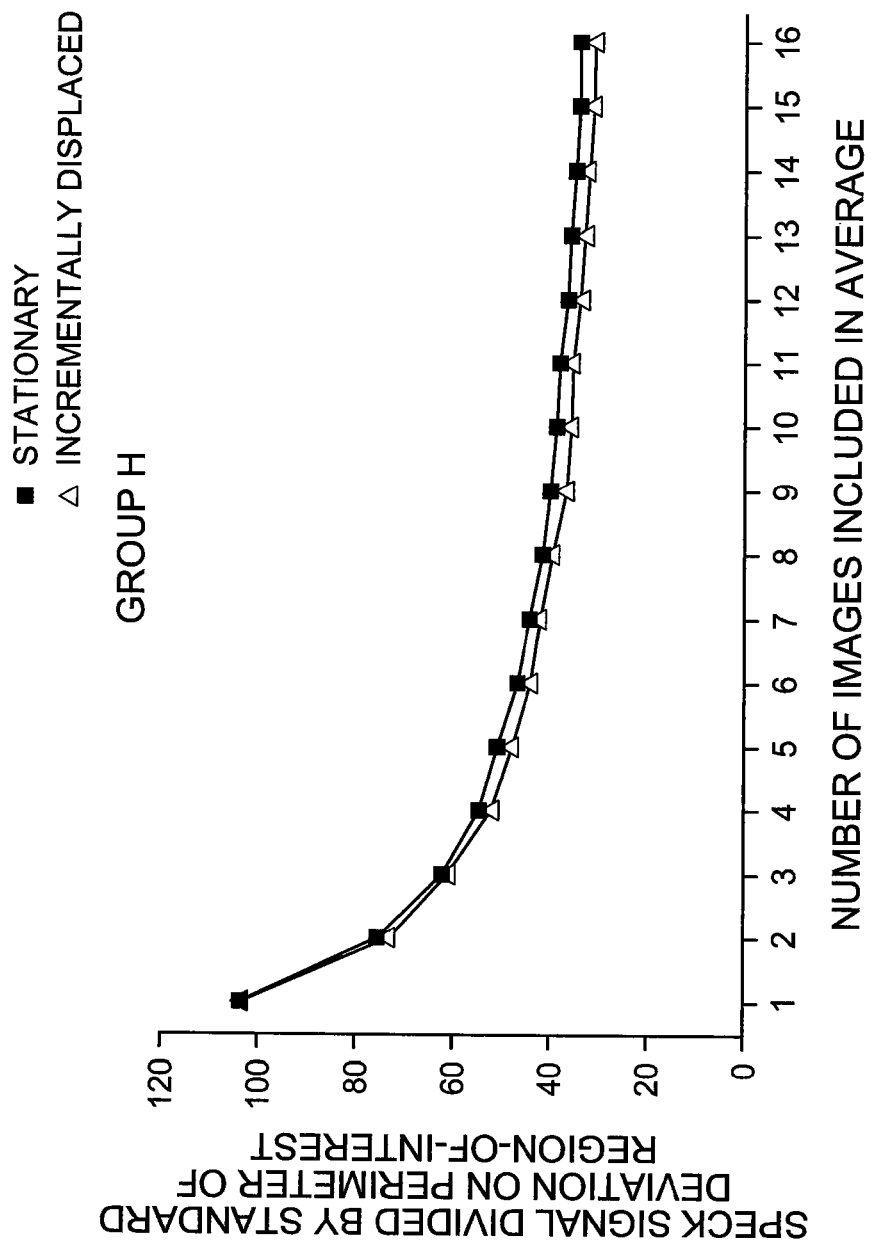

FIG. 16 is another graphical representation of the results of measurements of the image evaluation insert of FIG. 12 acquired by the system and method of FIGS. 4 to 7 in accordance with the present invention. FIG. 16 shows the denominators used in the figures-of-merit plotted in FIG. 15, namely the standard deviation of the digital counts in each pixel on the perimeter of the region of interest. The data show that the standard deviation of the digital counts in each pixel on the perimeter of the region of interest generally decreases (i.e., improves) with increasing number of images included in the image average, and furthermore that the standard deviation of the digital counts in each pixel on the perimeter of the region of interest generally decreases faster for the incrementally displaced phosphor screen compared to the stationary phosphor screen.

The invention has been described in detail with particular reference to certain preferred embodiments thereof, but it will be understood that variations and modifications can be effected within the spirit and scope of the invention.

PARTS LIST 10 film-based radiographic or autoradiographic imaging system
20 X-ray source
30 sample object stage
40 X-ray film cassette
50 film compartment
60 phosphor screen or plate
70 support frame
80 linear motion device
90 connecting rod
95 computer control system
100 radiographic or radioisotopic imaging system
102 X-ray source
104 sample object stage
106 programmable multispectral light source
108 fiber optic bundles
110 optical compartment
114 lens and camera system
116 communication and computer control system
118 display device
120 sample environment
122 access means/member
124 phosphor screen or plate
126 frame
128 sheet
130 linear motion device
132 connecting rod
200-520 steps of inventive methods
600 alumina specks
610 phosphor screen defects

What is claimed is:

1. A system for capturing a radiographic or autoradiographic image of an object, comprising: a support member adapted to receive the object in an immobilized state;
   a phosphor screen adapted to transduce ionizing radiation from the object to visible light;
   means for capturing an image using the visible light; and
   a device for moving the phosphor screen incrementally to facilitate reduction of phosphor screen mottle.

2. The system of claim 1, wherein the phosphor screen is moved between image captures.

3. The system of claim 2 wherein the means for capturing an image comprises film responsive to the visible light and the film is exposed after each incremental movement of the phosphor screen.

4. The system of claim 1, further comprising an X-ray source and means for turning the source on and off, wherein the phosphor screen is moved during single image capture and the source is turned off during movement of the screen.

5. The system of claim 1 wherein the means for capturing an image comprises a digital capture device responsive to the visible light; further comprising means for averaging a series of individual images of the immobilized object so as to blur phosphor screen mottle.

6. The system of claim 1 wherein the phosphor screen is moved between image captures through a distance larger than phosphor grain size of the screen but smaller than a difference between a physical size of phosphor screen and a field of view of the image, so as to blur phosphor screen mottle.

7. The system of claim 1, further comprising an X-ray source and means for turning the source on and off, wherein the phosphor screen is moved during single image capture and the source is turned off during movement of the screen through a distance larger than phosphor grain size of the screen but smaller than a difference between a physical size of the phosphor screen and a field of view of the image, so as to blur phosphor screen mottle.

8. A method for capturing a radiographic or autoradiographic image of an object, comprising:
   placing the object in an immobilized state on an object stage;
   capturing a series of images of the object via a phosphor screen adapted to transduce ionizing radiation from the object to visible light; and
   moving the phosphor screen incrementally to facilitate reduction of phosphor screen mottle.

9. The method of claim 8, wherein the phosphor screen is moved between image captures.

10. The method of claim 8, further comprising exposing the object to radiation from an X-ray source, moving the phosphor screen during single image capture and turning off the source during movement of the screen.

11. The method of claim 10, wherein the phosphor screen is moved between image captures through a distance larger than phosphor grain size of the screen but smaller than a difference between a physical size of the phosphor screen and a field of view of the image, so as to blur phosphor screen mottle.

12. The method of claim 8 wherein the images are captured on film responsive to the visible light and the film is exposed after each incremental movement of the phosphor screen.

13. The method of claim 8 wherein the images are captured digitally in response to the visible light, further comprising averaging the series of individual digital images of the immobilized object so as to blur phosphor screen mottle.

14. The method of claim 8 wherein the phosphor screen is moved between image captures through a distance larger than phosphor grain size of the screen but smaller than a difference between a physical size of the phosphor screen and a field of view of the image, so as to blur phosphor screen mottle.

15. A method for capturing multimodal images of an object, comprising:
   placing the object in an immobilized state on an object stage;
   positioning a phosphor screen in an image path from the object to transduce ionizing radiation passing through the object to visible light;
   capturing a series of images of the object using the visible light;
   moving the phosphor screen incrementally to facilitate reduction of phosphor screen mottle in the series;
   removing the phosphor screen from the image path; and
   capturing at least one optical image of the object.

16. The method of claim 15, wherein the phosphor screen is moved incrementally between image captures.

17. The method of claim 15, further comprising exposing the object to radiation from an X-ray source, moving the phosphor screen during single image capture and turning off the source during movement of the screen.

18. The method of claim 15 wherein the at least one optical image captured may be bright-field or dark-field from luminescence and fluorescence; and in the series, X-ray.

19. The method of claim 15 wherein the phosphor screen is moved between image captures of the series through a distance larger than a phosphor grain size of the screen and smaller than a difference between a physical size of the phosphor screen and a field of view of the image, so as to blur phosphor screen mottle.

20. The method of claim 15, further comprising exposing the object to radiation from an X-ray source, moving the phosphor screen incrementally during single image capture and turning off the source during movement of the screen, wherein the phosphor screen is moved through a distance larger than phosphor grain size of the screen but smaller than a difference between a physical size of the phosphor screen and a field of view of the image, so as to blur phosphor screen mottle.

21. The method of claim 15 wherein the series of images is captured digitally, further comprising averaging the series of individual images of the immobilized object so as to blur phosphor screen mottle.

22. A system for capturing multimodal images of an object, comprising:
    a support member adapted to receive the object in an immobilized state;
    a phosphor screen adapted to transduce ionizing radiation from the object to visible light;
    multimodal means for capturing X-ray or optical images of the object, or both;
    a device for incrementally moving the phosphor screen to facilitate reduction of phosphor screen mottle;
    a device for removing the phosphor screen from the image path for capturing optical images; and
    means for capturing at least one optical image of the object.

23. The system of claim 22, further comprising an X-ray source and means for turning the source on and off, wherein the phosphor screen is moved during single image capture and the source is turned off during movement of the screen.

24. The system of claim 22, wherein the phosphor screen is moved during image capture through a distance larger than phosphor grain size of the screen but smaller than a difference between a physical size of the phosphor screen and a field of view of the image, so as to blur phosphor screen mottle.

25. The system of claim 24 wherein the phosphor screen is moved between image captures through a distance larger than phosphor grain size of the screen but smaller than a difference between a physical size of phosphor screen and a field of view of the image, so as to blur phosphor screen mottle.

26. The system of claim 22, wherein the phosphor screen is moved incrementally between image captures.

27. The system of claim 22 wherein the means for capturing may be optical, X-ray or radioisotopic.

28. The system of claim 22 wherein the image captured may be bright-field or dark-field from luminescence and fluorescence, X-ray or radioisotopic.

29. The system of claim 22, wherein the means for capturing an X-ray image comprises film responsive to the visible light and the film is exposed after each incremental movement of the phosphor screen.

30. The system of claim 22, wherein the means for capturing an X-ray image comprises a digital capture device responsive to the visible light; and means for averaging a series of individual images of the immobilized object so as to blur phosphor screen mottle.

* * * * *